US010900850B2

(12) United States Patent
Andrews et al.

(10) Patent No.: US 10,900,850 B2
(45) Date of Patent: Jan. 26, 2021

(54) METHODS OF IMPROVING THE MEASUREMENT OF KNEE STRESS IN ION-EXCHANGED CHEMICALLY STRENGTHENED GLASSES CONTAINING LITHIUM

(71) Applicant: CORNING INCORPORATED, Corning, NY (US)

(72) Inventors: Ryan Claude Andrews, Elmira, NY (US); Rostislav Vatchev Roussev, Painted Post, NY (US); Vitor Marino Schneider, Painted Post, NY (US)

(73) Assignee: CORNING INCORPORATED, Corning, NY (US)

( * ) Notice: Subject to any disclaimer, the term of this patent is extended or adjusted under 35 U.S.C. 154(b) by 289 days.

(21) Appl. No.: 16/015,776

(22) Filed: Jun. 22, 2018

(65) Prior Publication Data
US 2019/0033144 A1    Jan. 31, 2019

Related U.S. Application Data

(60) Provisional application No. 62/538,335, filed on Jul. 28, 2017.

(51) Int. Cl.
*G01L 1/24* (2006.01)
*G01N 21/43* (2006.01)
(Continued)

(52) U.S. Cl.
CPC .............. *G01L 1/24* (2013.01); *C03C 21/002* (2013.01); *G01N 21/23* (2013.01); *G01N 21/43* (2013.01);
(Continued)

(58) Field of Classification Search
CPC .......... G01L 1/24; C03C 21/002; G01N 21/23; G01N 21/43; G01N 21/552; G01N 33/386
(Continued)

(56) References Cited

U.S. PATENT DOCUMENTS

| 4,400,052 A | 8/1983 | Alferness et al. |
| 6,396,576 B1 | 5/2002 | Bleyle |

(Continued)

FOREIGN PATENT DOCUMENTS

| CN | 105705936 A | 6/2016 |
| JP | 2004271360 A | 9/2004 |

(Continued)

OTHER PUBLICATIONS

International Searching Authority Invitiation to Pay Additional Fees PCT/US2018/043877 dated Nov. 30, 2018.

(Continued)

*Primary Examiner* — Max H Noori
(74) *Attorney, Agent, or Firm* — Kevin M. Johnson

(57) ABSTRACT

Methods of improving the measurement of knee stress in an ion-exchanged chemically strengthened Li-containing glass sample that includes a knee are disclosed. One of the methods includes compensating for a shift in the location of the TIR-PR transition location associated with the critical angle location, wherein the shift is due to the presence of a leaky mode. Another method includes applying select criteria to the captured mode spectra image to ensure a high-quality image is used for the knee stress calculation. Another method combines direct and indirect measurements of the knee stress using the mode spectra from multiple samples to obtain greater accuracy and precision as compared to using either the direct measurement method or the indirect measurement method alone. Quality control methods of forming
(Continued)

the glass samples using measured mode spectra and related techniques for ensuring an accurate measurement of the knee stress are also disclosed.

59 Claims, 11 Drawing Sheets

(51) Int. Cl.
*G01N 33/38* (2006.01)
*G01N 21/23* (2006.01)
*C03C 21/00* (2006.01)
*G01N 21/552* (2014.01)

(52) U.S. Cl.
CPC ......... *G01N 21/552* (2013.01); *G01N 33/386* (2013.01)

(58) Field of Classification Search
USPC .......................................................... 73/763
See application file for complete search history.

(56) References Cited

U.S. PATENT DOCUMENTS

| | | | |
|---|---|---|---|
| 7,583,368 B1* | 9/2009 | Simpson | G01L 1/241 356/35.5 |
| 8,854,623 B2 | 10/2014 | Fontaine et al. | |
| 8,873,028 B2 | 10/2014 | Sheldon et al. | |
| 8,957,374 B2 | 2/2015 | Liu et al. | |
| 9,140,543 B1 | 9/2015 | Allan et al. | |
| 9,442,028 B2 | 9/2016 | Roussev et al. | |
| 9,487,434 B2 | 11/2016 | Amin et al. | |
| 9,544,981 B2 | 1/2017 | Zhang et al. | |
| 9,696,207 B2 | 7/2017 | Roussev et al. | |
| 9,897,574 B2 | 2/2018 | Andrews et al. | |
| 2010/0267163 A1 | 10/2010 | Ran et al. | |
| 2014/0092377 A1 | 4/2014 | Liu et al. | |
| 2014/0368808 A1 | 12/2014 | Roussev et al. | |
| 2015/0066393 A1 | 3/2015 | Liu et al. | |
| 2016/0178477 A1 | 6/2016 | Roussev et al. | |
| 2016/0356760 A1 | 12/2016 | Roussev et al. | |
| 2017/0082577 A1 | 3/2017 | Roussev et al. | |
| 2019/0170609 A1* | 6/2019 | Taverner | G02B 6/03694 |
| 2019/0301952 A1* | 10/2019 | Andrews | G01N 21/43 |
| 2020/0102243 A1* | 4/2020 | Li | H05K 5/0017 |

FOREIGN PATENT DOCUMENTS

| | | |
|---|---|---|
| WO | 2017053853 A2 | 3/2017 |
| WO | 2017115811 A1 | 7/2017 |

OTHER PUBLICATIONS

International Search Report and Written Opinion PCT/US2018/043877 dated Jan. 24, 2019, 26 Pgs.

Rigrod et al. "index profile determination of heterostructure GaAs planar waveguides from mode-angle measurements at 10.6 um wavelength", Journal of the Optical Society of American, 65(1) 1975, pp. 46-55.

Chandler et al. "A new approach to the determination of planar waveguide profiles by means of a non-stationary mode index calculation" Optica Acta. 33(2) 1986, pp. 127-143.

Cleveland; "Robust Locally Weighted Regression and Smoothing Scatterplots"; Journal of the American Statistical Association; 74: 368 (1979) pp. 829-836.

Chinese Patent Application No. 201810851867.6, Office Action dated Sep. 27, 2020, 21 pages (11 pages of English Translation and 10 pages of Original Document); Chinese Patent Office.

* cited by examiner

METHODS OF IMPROVING THE MEASUREMENT OF KNEE STRESS IN ION-EXCHANGED CHEMICALLY STRENGTHENED GLASSES CONTAINING LITHIUM

CROSS-REFERENCE TO RELATED APPLICATIONS

This application claims the benefit of priority under 35 U.S.C. § 119 of U.S. Provisional Application Ser. No. 62/538,335 filed on Jul. 28, 2017, the content of which is relied upon and incorporated herein by reference in its entirety.

FIELD

The present disclosure relates to chemically strengthened glass, and in particular relates to methods of improving the measurement of knee stress in ion-exchanged chemically strengthened glasses containing lithium.

BACKGROUND

Chemically strengthened glasses are glasses that have undergone a chemical modification to improve at least one strength-related characteristic, such as hardness, resistance to fracture, etc. Chemically strengthened glasses have found particular use as cover glasses for display-based electronic devices, especially hand-held devices such as smart phones and tablets.

In one method, the chemical strengthening is achieved by an ion-exchange process whereby ions in the glass matrix are replaced by externally introduced ions, e.g., from a molten bath. The strengthening generally occurs when the replacement ions (i.e., in-diffusing ions) are larger than the native ions (e.g., Na+ ions replaced by K+ ions). The ion-exchange process gives rise to a refractive index profile that extends from the glass surface into the glass matrix. The refractive index profile induced by potassium has a depth-of-layer or DOL that defines a size, thickness or "deepness" of the ion-diffusion layer as measured relative to the glass surface. Said index profile also correlates with a number of stress-related characteristics, including stress profile, surface stress, center tension, knee stress, birefringence, etc. The refractive index profile may define an optical waveguide when the profile meets certain criteria.

Recently, chemically strengthened glasses with a very large depth of compression (DOC) have been shown to have superior resistance to fracture upon face drop on a hard rough surface. Glasses that contain lithium ("Li-containing glasses") can allow for fast ion exchange (e.g., Li+ exchange with Na+ or K+) to obtain a large DOC. Note that in such glasses DOC does not necessarily correspond to the potassium-defined DOL, and is in many cases much larger than that DOL.

An example stress profile of particular commercial importance includes first region near the substrate surface characterized by rapid or "spike" change in refractive index and stress and a second region deeper in the substrate where the refractive index can vary slowly and can be substantially the same as the bulk refractive index. The location where the first and second regions of the profile meet is called the knee because the stress profile curve at the transition between the two regions has a knee-shaped sudden change in slope. The spike portion of the profile is particularly helpful in preventing fracture when glass is subjected to force on its edge (e.g., a dropped smart phone) or when the glass experiences significant bending. The spike can be achieved in Li-containing glasses by ion exchange in a bath containing $KNO_3$.

It is often preferred that the spike be obtained in a bath having a mixture of $KNO_3$ and $NaNO_3$ so that Na+ ions are also exchanged. The Na+ ions diffuse faster than K+ ions and thus diffuse at least an order of magnitude deeper than the K+ ions. Consequently, the deeper section region of the profile is formed mainly by Na+ ions and the shallow portion of the profile is formed mainly by K+ ions.

Because the Na for Li exchange does not produce a substantial increase in the refractive index, the deeper second region of the profile usually does not support guided modes, i.e., does not define a waveguide. Furthermore, in lithium containing glasses similar to the Li-containing Corning Gorilla® 5 glass, compressive stress induces a relative refractive index decrease for the component parallel to the stress, which leads to decrease of the relative refractive index of the transverse electric (TE) optical wave in a chemically strengthened glass sheet.

For chemically strengthened Li-containing glasses to be commercially viable as cover glasses and for other applications, their quality during manufacturing must be controlled to certain specifications. This quality control (QC) depends in large part on the ability to control the ion-exchange process during manufacturing, which requires the ability to quickly and non-destructively measure important parameters of the refractive index and stress profiles, and in particular the knee stress CSk, which occurs at the knee of the profile where distribution of K ions exchanged into the substrate abruptly tapers off to a region in the substrate where the local compressive stress is generated substantially by Na ions diffused into the glass.

Presently, direct measurements of the knee stress CSk are particularly difficult in cases where the second region does not support guided waves. Direct measurements can also be adversely affected by measurement conditions such as sample warpage, illumination non-uniformities, and reduced image quality of the captured mode spectra. In addition, the presence of guided or leaky modes very close to the critical angle can reduce the measurement conditions (measurement window) for adequately determining the critical angle, which is the location where total-internal reflection (TIR) transitions to partial reflection (PR). This location is needed to accurately determine the knee stress CSk by the direct method. The inability to adequately characterize the knee stress CSk over a relatively wide measurement window has hindered the manufacturing of chemically strengthened Li-containing glasses because the knee stress is a key parameter used in quality control when forming chemically strengthened Li-based glass products with superior drop-fracture resistance, such as Gorilla® glass made by Corning, Inc., of Corning, N.Y.

SUMMARY

Methods of performing non-destructive, direct measurements of the knee stress CSk are disclosed in U.S. Patent Application Publication No. 2016/0356760, while methods of performing non-destructive indirect measurements of the knee stress CSk are disclosed in U.S. Patent Application Publication No. 2017/0082577 (issued as U.S. Pat. No. 9,897,574), all of which are incorporated by reference herein.

As noted above, a major limitation of the previously disclosed direct method of measuring CSk is a limited measurement window or "sweet spot." In the preferred measurement window, both the TM and TE effective indices at the depth of the knee are relatively far away from effective indices associated with TM and TE guided and leaky modes, which allows one to obtain an accurate determination of the critical angle location, as described below.

Another limitation that occurs particularly in some cases of prism-coupling angular spectra after first-step chemical strengthening, is the relatively poor precision of detecting the critical angle for the TE mode, even when the spectrum is in the "sweet spot." One of the indirect methods based the spike-stress-slope can avoid these issues, but its precision becomes inadequate when the spike slope is very high (such as >60 MPa/micron), which is characteristic of most currently practiced second-step profiles near the surface. Furthermore, this method is only accurate when the TM (the upper) transition is strictly in the "sweet spot," otherwise a significant systematic error can be induced.

In addition, the double-ion-exchange (DIOX) process complicates the extraction of CSk by using the stress-slope-method because the sweet spot is small and because the DIOX process introduces significant uncertainty in the extrapolation of the estimated slope beyond the highest-order mode to the critical-angle index.

The indirect method based on utilizing the relationship between CSk and the birefringence of the highest-order guided mode suffers from significant systematic errors when the conditions of chemical strengthening deviate substantially from a reference condition. It has been found that this is problematic for manufacturing operations that are focused on minimizing cost and that utilize unskilled labor. In most cases, the restrictions on the fabrication process and product attributes imposed by the requirement for validity of CSk measurements by this method are much tighter than the restrictions dictated by the mechanical-performance requirements. Usually these tight restrictions for QC metrology validity are viewed by the strengthening operations as unnecessary and costly.

The ideal method for measuring CSk for QC is nondestructive, fast, precise, and accurate, and has at best only small systematic errors over a range of measurement conditions (i.e., over a large measurement window) so that an out-of-specification product (sample) does not pass for an in-specification product (sample) by a combination of systematic errors that makes it appear in-specification.

The present disclosure is thus directed to methods of improving the precision and accuracy of the direct method of measuring CSk of chemically strengthened glass samples formed by ion-exchange and containing lithium. In particular, the methods widen the "sweet spot" for such glass samples where the accuracy of the method is considered good. Furthermore, methods of QC are disclosed that take advantage of the improved direct method of CSk measurement and use the improved direct methods in combination with an indirect method to improve the overall CSk measurement.

In one aspect of the disclosure, methods of direct CSk measurement are disclosed, where one or more sources of systematic, random, and quasi-random error are mitigated, allowing for more precise direct measurements of CSk within the previously defined "sweet spot," and in addition, widening of the range of angular coupling spectra over which direct-CSk measurements with acceptable accuracy and precision are enabled. This effectively widens the measurement window to almost the full range of possible angular-coupling spectra, with only very narrow regions of spectral space in which direct CSk measurements are less reliable and subject to larger errors.

The methods disclosed herein are generally directed to making measurements of the knee stress CSk for chemically strengthened Li-containing glasses having a stress profile that has a knee. Such a profile is produced by an ion-exchange process whereby Li+ (the native ion) is exchanged with (in-diffusing) K+ and Na+ ions (i.e., Li+⇔K+, Na+). An example of a stress profile having a knee includes a first region adjacent the substrate surface and that is spiked (and thus is also referred to the spike region or just "spike") and a second region that is more gradual (e.g., has a much smaller slope of stress with depth, and may be approximated as following a power law) in a larger portion of the interior ("deep region") of the substrate. The knee is defined by the relatively abrupt transition between the first and second regions. The spike is generally formed by the slower diffusion (and thus shallower) K+ ions while the deeper region is formed by the faster (and thus deeper) diffusing Na+ ions.

Another aspect of the methods disclosed herein is directed to performing QC of the glass samples being processed. Such quality control is important for a commercially viable manufacturing process. The QC methods include adjusting the DIOX process parameters for fabricating IOX articles based on measurements of the knee stress CSk of fabricated IOX articles.

Another aspect of the disclosure is a method of improving a measurement of knee stress CSk in a chemically strengthened Li-containing glass sample having a warped surface and a body and that includes a stress profile having a knee. The method comprises: capturing an image of at least one of a TE mode spectrum and a TM mode spectrum; measuring a slope of light intensity at a transition between the total-internal reflection and the partial-internal reflection sections of the mode spectrum (i.e., the TIR-PR transition) and measuring a width of the TIR-PR transition for at least one of the TE mode spectrum and TM mode spectrum; and comparing the measured slope and the measured width to a slope threshold and a width threshold $WT_{TIR-PR}$ associated with reference glass sample having a flat surface.

Another aspect of the disclosure is a method of improving a measurement of knee stress CSk in a chemically strengthened Li-containing glass sample having a surface and a body and that includes a stress profile having a knee and that defines a waveguide that supports light as guided waves and a leaky mode. The method comprises: capturing an image of a TE mode spectrum and a TM mode spectrum of the guide waves and leaky mode; measuring a position of maximum slope of a transition between a total-internal reflection and a partial-internal reflection (TIR-PR) for the light supported in the waveguide for each of the TE mode spectrum and the TM mode spectrum; determining from the TE and TM mode spectra a position of the leaky mode as a relative minima after the TIR-PR transition; determining from the leaky mode position an amount of shift in the TIR-PR position caused by the leaky mode; adding the amount of shift from the measured position of the TIR-PR transition to arrive at a corrected TIR-PR transition location; and using the corrected TIR-PR transition location to determine the knee stress.

Another aspect of the disclosure is a method of improving a measurement of a knee stress in a chemically strengthened Li-containing glass sample having a surface and a body and that includes a stress profile having a knee and that defines a waveguide that supports light as guided modes. The method comprises: capturing an image of a TE mode spectrum and a TM mode spectrum; measuring a slope of a transition between a total-internal reflection and a partial-internal reflection (TIR-PR) for the light supported by the waveguide for each of the TE mode spectrum and the TM mode spectrum; and comparing the slope to a steepness threshold STH and using the slope to determine a location of the TIR-PR transition and using the corrected TIR-PR transition location to determine the knee stress only if the slope is greater than the select steepness threshold.

Another aspect of the disclosure is a method of measuring a knee stress in chemically strengthened Li-containing glass samples each having a surface and a body and that includes a stress profile having a knee and that defines a waveguide that supports light as guided modes in the spike region which has a monotonically decreasing index profile. The method includes: measuring TE and TM mode spectra for each of the multiple glass samples; for each of the measured TE and TM mode spectra, directly measuring a knee stress $CSk^{direct}$ and also indirectly measuring the knee stress via $CSk^{direct} = \beta_x \cdot F_4$, where $\beta_x$ is a last-mode birefringence and $F_4$ is a scaling factor; calculating a moving average $F_4^{average}$ for the scaling factor $F_4$ using the directly measured knee stresses $CSk^{direct}$ via the relationship $F_4 = CSk^{direct}/\beta_x$; and calculating a hybrid knee stress $CSk^{hybrid} = \beta_x \cdot F_4^{average}$.

Another aspect of the disclosure is a method of ensuring an accurate measurement of knee stress in a chemically strengthened Li-containing glass sample having a surface and a body and that includes a stress profile having a knee and that defines a waveguide that supports light as guided modes. The method includes: capturing TE mode spectrum and a TM mode spectrum respectively comprising TE fringes and TM fringes; measuring a slope SLP of a transition between a total-internal reflection and a partial-internal reflection (TIR-PR) for the light supported by the waveguide for each of the TE mode spectrum and the TM mode spectrum; and comparing the slope to a steepness threshold STH and using the slope to determine a a location of the TIR-PR transition and using the corrected TIR-PR transition location to determine the knee stress only if the slope is greater than the select steepness threshold STH.

Another aspect of the disclosure is a method of ensuring an accurate measurement of knee stress in a chemically strengthened Li-containing glass sample having a surface and a body and that includes a stress profile having a knee and that defines a waveguide that supports light as guided modes. The method includes: irradiating the glass sample by directing light from a light source as a light beam through a coupling prism and to the surface of the sample to generate an angular illumination spectrum; detecting the angular illumination spectrum at a digital sensor to capture TE mode spectrum and a TM mode spectrum respectively comprising TE fringes and TM fringes and respective total-internal reflection and a partial-internal reflection (TIR-PR) transitions associated with a critical angle and that define respective critical angle effective index values $n_{crit}^{TE}$ and $n_{crit}^{TM}$; measuring an intensity gradient in the angular illumination spectrum in the vicinity of the TIR-PR transitions; and proceeding with the measurement of the knee stress only if the measured intensity gradient is less than an intensity gradient threshold.

Another aspect of the disclosure is method of performing quality control of an IOX process used to form chemically strengthened Li-containing glass samples having a surface and a body and that includes a stress profile having a spike and a knee and that defines a waveguide that supports light as guided modes. The method includes: for each of a plurality of glass samples formed by the IOX process, measuring TE and TM mode spectra of the guided modes for each of the glass samples; comparing the measured TE and TM mode spectra to reference TE and TM mode spectra of at least one reference glass sample formed using the same IOX process and having a flat surface; and adjusting the IOX process to maintain the measured TE and TM mode spectra to be within at least one mode spectrum tolerance of the reference TE and TM mode spectra. The adjustment can include one or more of changing the diffusion temperature, the diffusion time and the ion concentration of either or both of the in-diffusing ions, which in an example are K+ and N+.

Additional features and advantages are set forth in the Detailed Description that follows, and in part will be apparent to those skilled in the art from the description or recognized by practicing the embodiments as described in the written description and claims hereof, as well as the appended drawings. It is to be understood that both the foregoing general description and the following Detailed Description are merely exemplary, and are intended to provide an overview or framework to understand the nature and character of the claims.

BRIEF DESCRIPTION OF THE DRAWINGS

The accompanying drawings are included to provide a further understanding, and are incorporated in and constitute a part of this specification. The drawings illustrate one or more embodiment(s), and together with the Detailed Description serve to explain principles and operation of the various embodiments. As such, the disclosure will become more fully understood from the following Detailed Description, taken in conjunction with the accompanying Figures, in which.

DETAILED DESCRIPTION

Reference is now made in detail to various embodiments of the disclosure, examples of which are illustrated in the accompanying drawings. Whenever possible, the same or like reference numbers and symbols are used throughout the drawings to refer to the same or like parts. The drawings are not necessarily to scale, and one skilled in the art will recognize where the drawings have been simplified to illustrate the key aspects of the disclosure.

The claims as set forth below are incorporated into and constitute part of this Detailed Description.

The term "IOX article" and "glass sample" are used interchangeably herein.

In the discussion below, the transition between total-internal reflection and partial-internal reflection in a given mode spectrum is referred to as the TIR-PR transition, and the location of the TIR-PR transition is referred to as the TIR-PR location.

The terms "ion exchange" and "ion exchanged" are both represented by the acronym IOX, and it will be apparent from the context of the discussion which term applies. The acronym DIOX means either "double ion exchange" or "double ion exchanged."

The acronyms TE and TM respectively stand for "transverse electric" and "tranverse magnetic" and refer to the direction of the electric and magnetic fields of the guided waves supported by the IOX region formed in the glass substrate as described below. The TE and TM guided waves are also referred to below as "TM waves" and "TE waves."

Figure 3A:
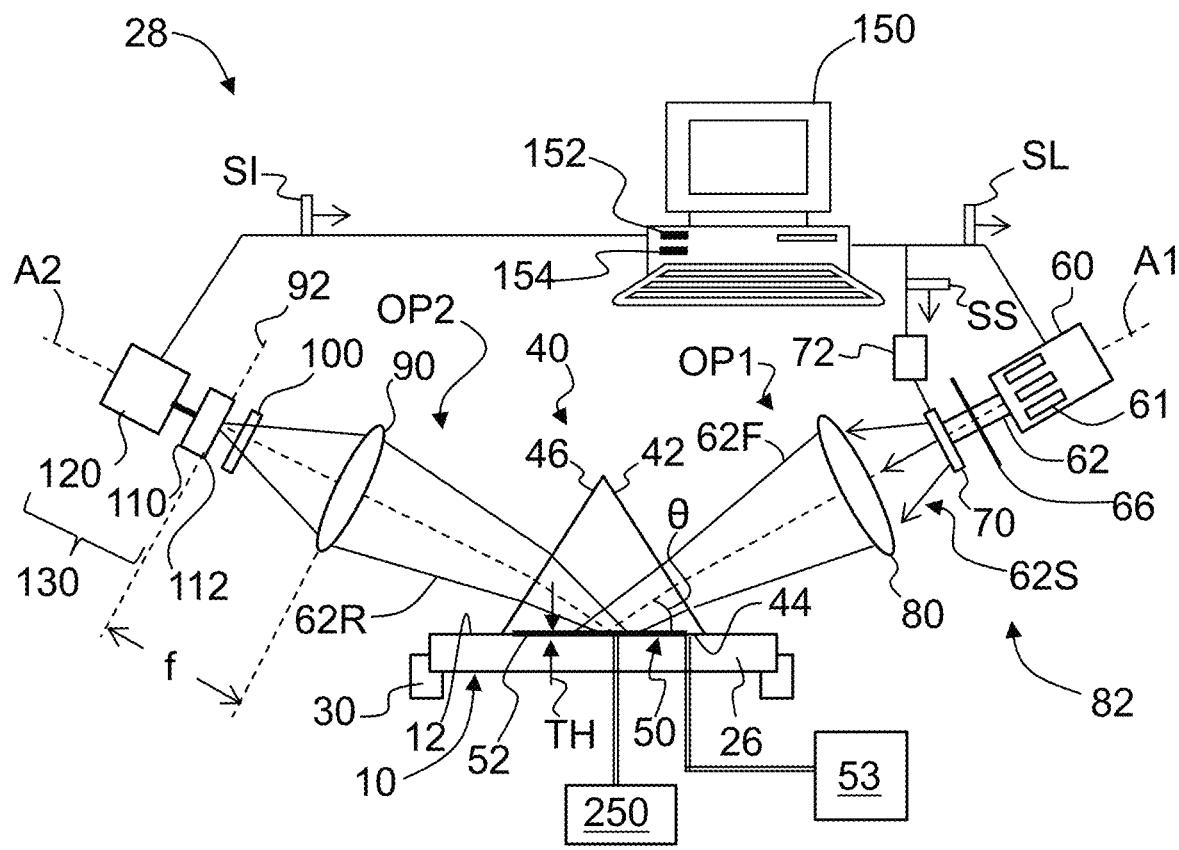
FIG. 3A is a schematic diagram of an example prism-coupling system according to the disclosure and that is used to measure IOX articles using the methods disclosed herein.
Figure 3B:
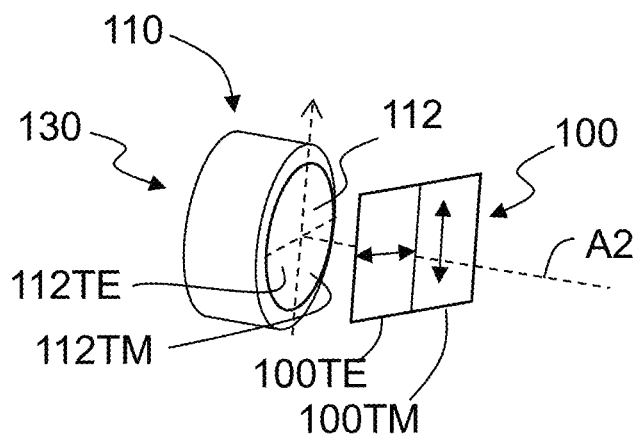
FIG. 3B is a close-up view of the photodetector system of the prism-coupling system of FIG. 3A.
Figure 3C:
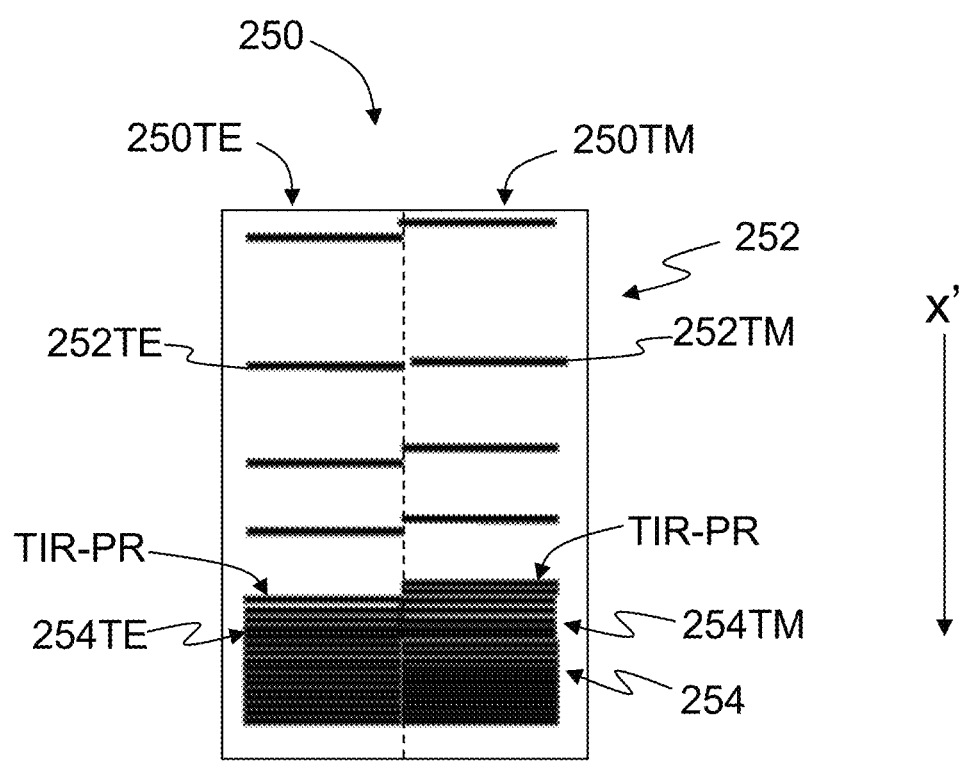
FIG. 3C is a schematic representation of an example measured mode spectrum.
Figure 3D:
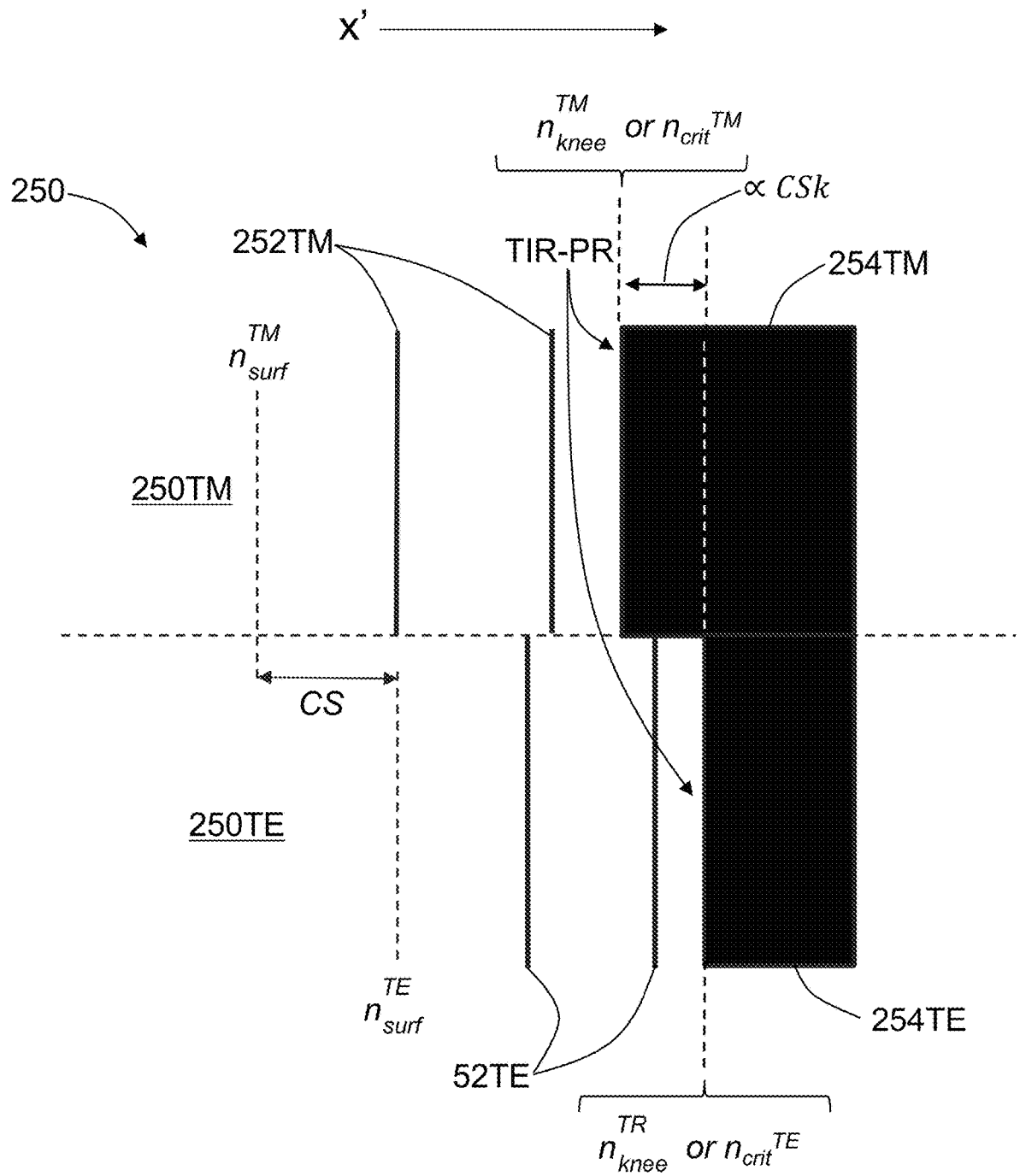
FIG. 3D is a schematic representation of an example measured mode spectrum of a Li-containing glass formed by an ion-exchange process using a mixture of $NaNO_3$ and $KNO_3$, with the mode spectrum including TM (top) and TE spectra (bottom), and also showing profile measurement parameters as explained below.
Figure 3E:
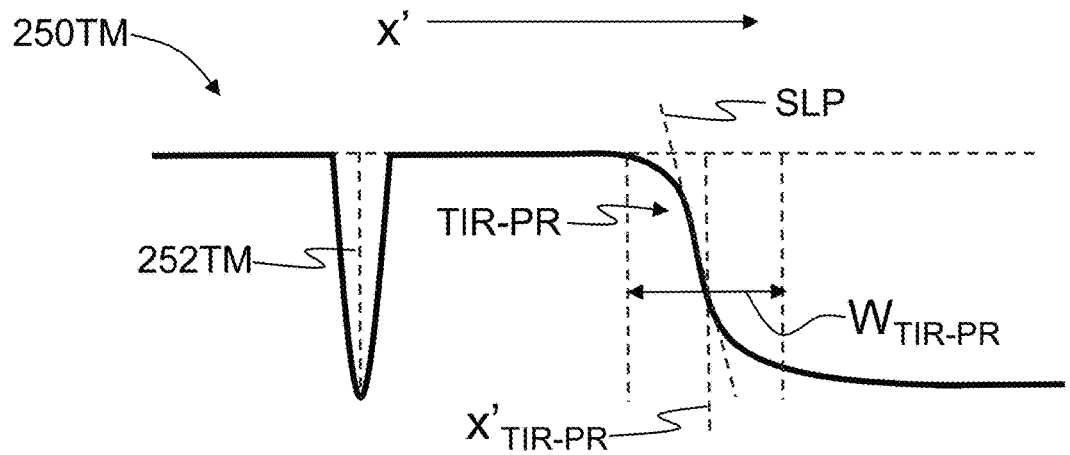
FIGS. 3E through 3G are schematic diagrams of a portion of an example TM mode spectrum illustrating how the location of the transition between total-internal reflection and partial-internal reflection (i.e., the TIR-PR location) can shift due to the presence of a leaky mode close to the TIR-PR location.

The term "resonance" is another word for a fringe in a mode spectrum, since the intensity distribution of a fringe has the shape of a resonance curve as known in the art and can have either an intensity peak or an intensity dip, depending on the measurement configuration of the prism coupling system that captures the TM or TE mode spectra (see, e.g., FIG. 3E and the mode fringe 252TM).

The terms "slope threshold" and "steepness threshold" are synonymous as used herein.

Example IOX Process in Li-based Glass

Figure 1A:
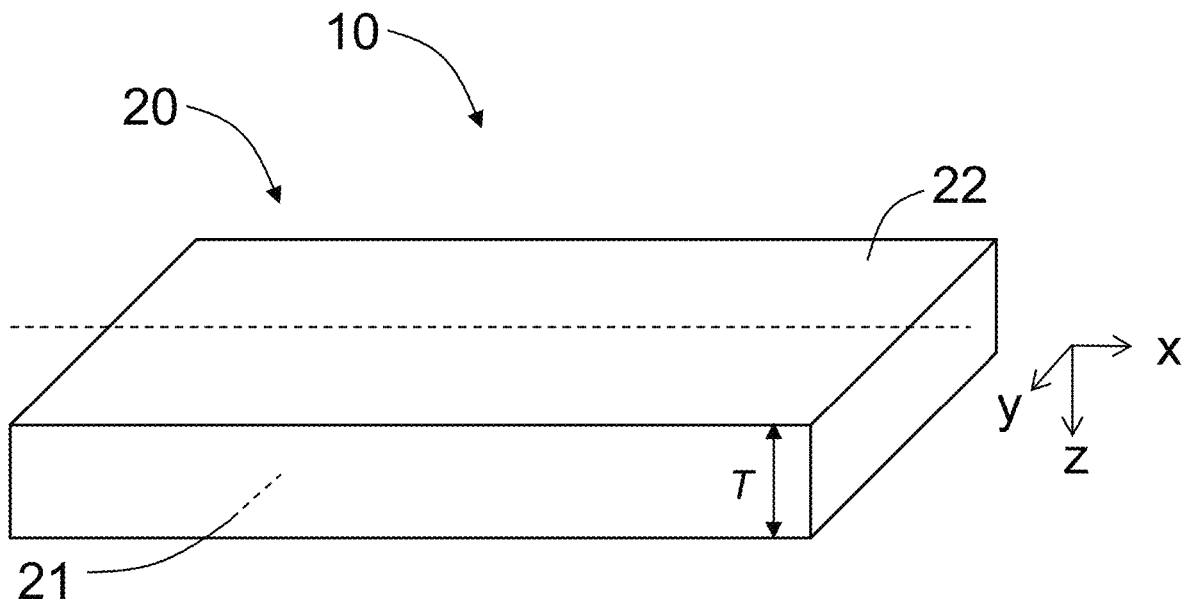
FIG. 1A is an elevated view of an example Li-containing glass substrate in the form of a planar substrate, into which ion exchange of both K ions and Na ions is performed.
Figure 1B:
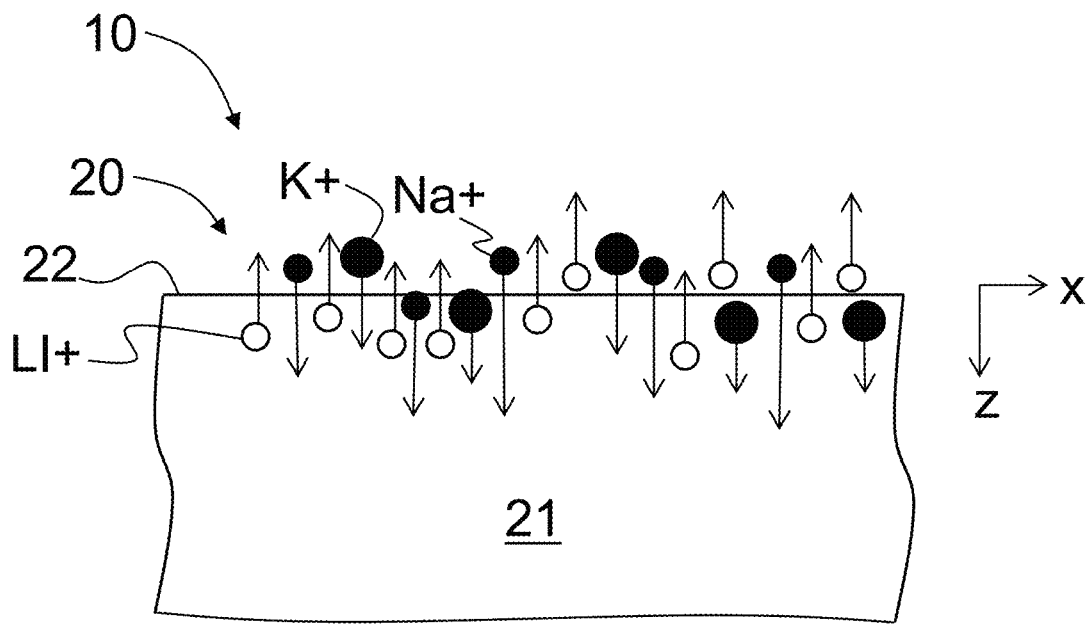
FIG. 1B is a close-up cross-sectional view of the ion exchanged substrate of FIG. 1A as taken in the x-z plane and that illustrates the K and Na ion-exchange process that takes place across the substrate surface and into the body of the substrate.

FIG. 1A is an elevated view an example IOX article 10 formed from a glass substrate 20 using an IOX process. The example glass substrate 20 is planar and has a body 21 and a (top) surface 22, wherein the body has a base (bulk) refractive index $n_s$, a surface refractive index $n_0$ and a thickness T in the z-direction. FIG. 1B is a close-up cross-sectional view of the glass substrate 20 as taken in the y-z plane and illustrates an example IOX process that takes place across surface 22 and into body 21 in the z-direction to define an IOX substrate 20 that constitutes the IOX article 10. The body 21 is constituted by the glass matrix of the IOX substrate.

In an example, the IOX articles 10 are formed using a DIOX process in a Li-containing glass. In one example, the DIOX process utilizes two different types of ions, namely Na+ and K+, to replace another different ion Li+ that is part of the glass body 21. The Na+ and K+ ions can be introduced into the glass body 21 either sequentially or concurrently using known IOX techniques, and may be introduced concurrently in one or more IOX steps. As noted above, the Na+ ions diffuse faster than the K+ ions and thus go deeper into the glass body 21. In other words, an example DIOX process in the present disclosure means that both K+ and Na+ were introduced in the glass during ion exchange, and does not necessarily mean that two IOX steps were performed.

Figure 1C:
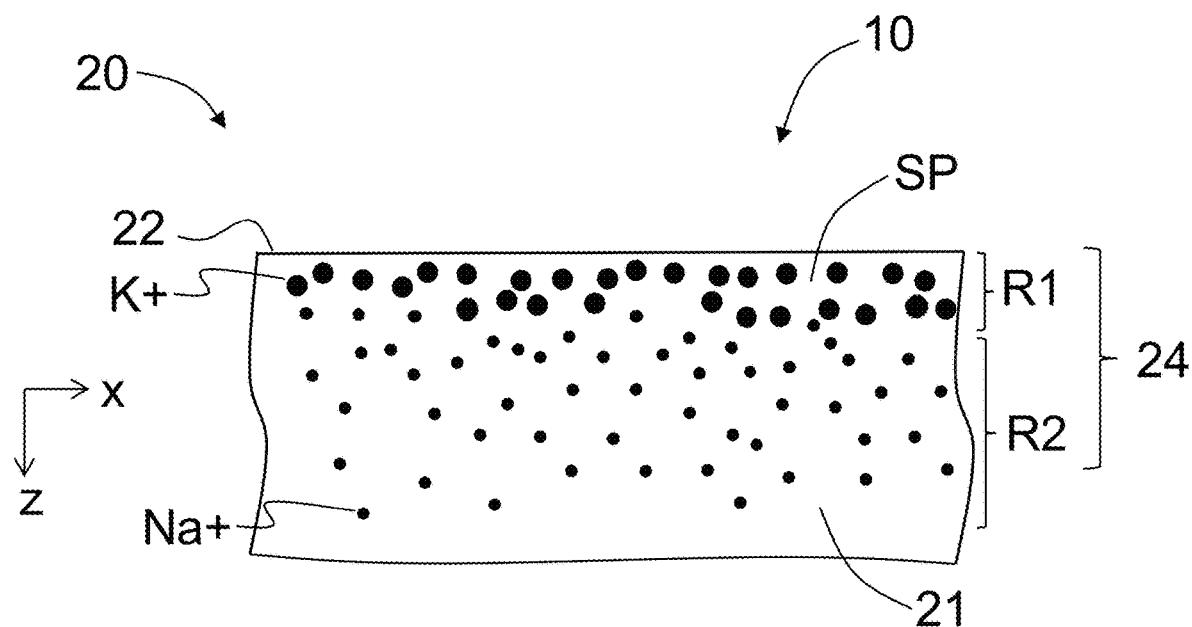
FIG. 1C schematically illustrates the result of the ion exchange process that forms the ion-exchanged substrate.
Figure 2A:
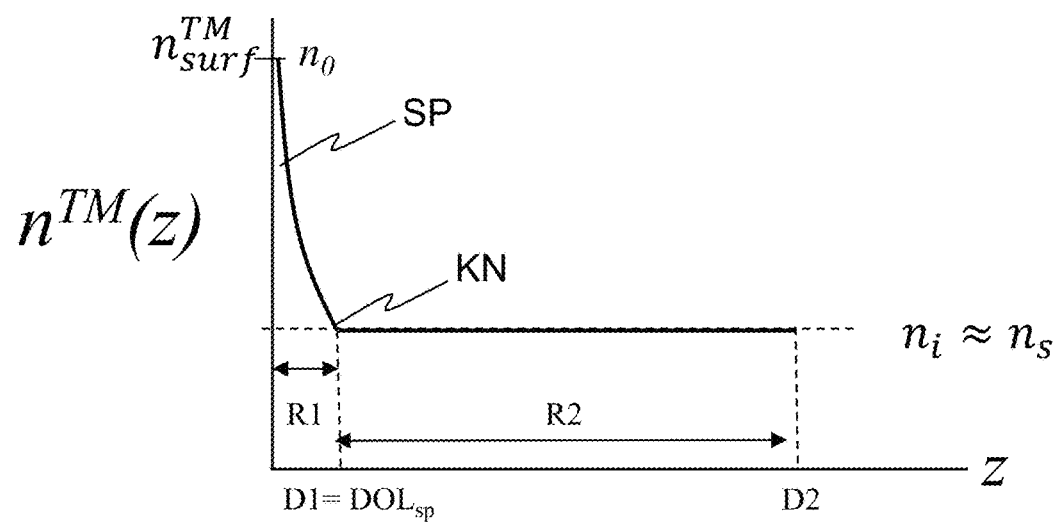
FIG. 2A is a representation of an example refractive index profile $n^{TM}(z)$ for the ion exchange substrate illustrated in FIG. 1C for the TM polarization.
Figure 2B:
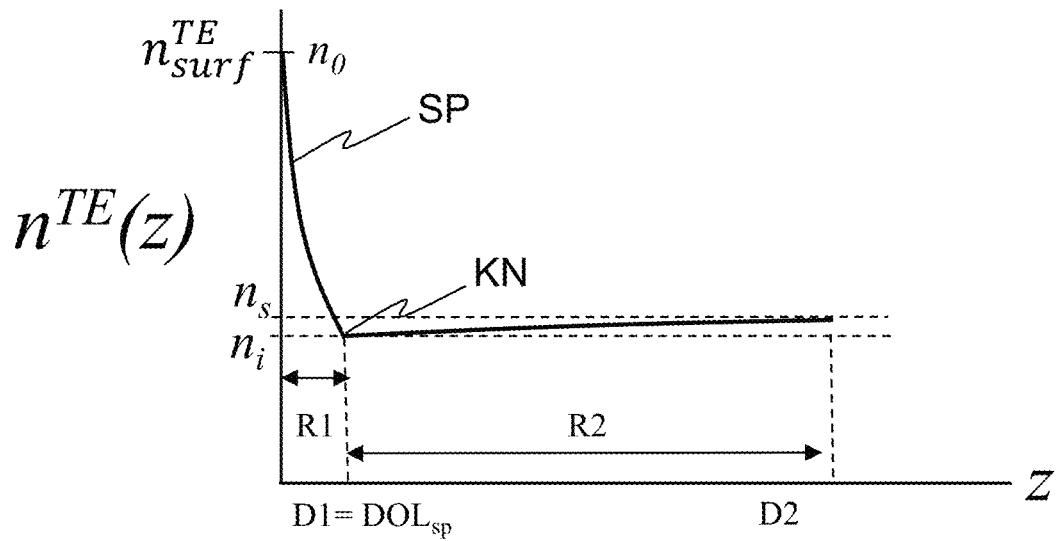
FIG. 2B is the same plot as FIG. 2A, but for the $n^{TE}(z)$, i.e., for the TE polarization.
Figure 2C:
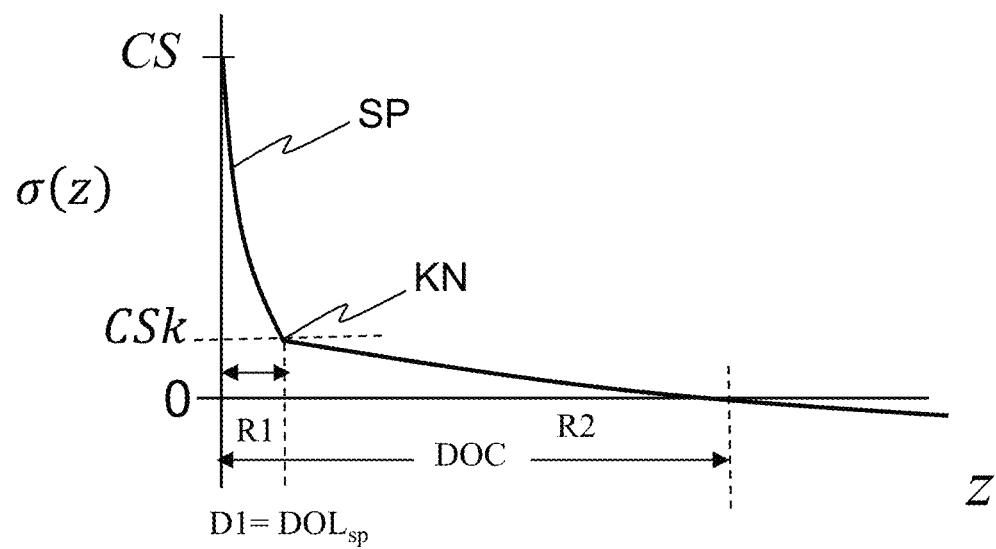
FIG. 2C is a plot of the stress $\sigma(z)$ versus the depth coordinate z for the corresponding refractive index profiles of FIGS. 2A and 2B and shows the spike (SP), the knee (KN) and the depth of compression (DOC)

FIG. 1C is a schematic diagram of the resulting DIOX process, and FIGS. 2A and 2B are representative example refractive index profiles $n^{TM}(z)$ and $n^{TE}(z)$ for the TM and TE polarizations, respectively, for the IOX substrate 20 having undergone the DIOX process such as shown in FIG. 1C. The associated stress profile can be represented by $\sigma(z)$ and is shown in FIG. 2C.

The IOX process defines an IOX region 24 in the glass body 21. The refractive index profile n(z) and the IOX region 24 each includes a first "spike" region R1 associated with the shallower ion-exchange (K+ ions) and that has a depth D1 into body 21 that defines a "depth-of-layer for the spike" denoted hereinafter as $DOL_{sp}$, or simply DOL. In the present disclosure the acronym DOL is used exclusively to mean $DOL_{sp}$ unless specified explicitly otherwise. The refractive index profile n(z) also includes a second region R2 associated with the deeper ion-exchange (Na+ ions) and that has a depth D2 that may extend all the way to the middle of the substrate. A knee KN is located at the bottom of the transition between the first region R1 and the second region R2. The stress profile of FIG. 2C also includes the first and second regions R1 and R2 and the knee KN, and also shows the depth of compression DOC extending from the substrate surface (z=0) into the second region R2. The refractive indices at the surface 22 of the substrate 20 due to the ion-exchange process for the TM and TE polarizations respectively denoted $n_{surf}^{TM}$ and $n_{surf}^{TE}$. Note that the refractive index profiles $n^{TM}(z)$ and $n^{TE}(z)$ are the effective indices associated with a waveguide defined by the spike SP in the glass substrate 20.

The deeper second region R2 may be produced in practice prior to the shallower first region R1, or at the same time as the shallower region. The region R1 is adjacent substrate surface 22 and is relatively steep and shallow and defining the spike SP, whereas region R2 is less steep and extends relatively deep into the substrate to the aforementioned depth D2 that is very large, and may be as deep as the middle of the substrate thickness. In an example, the region R1 has a maximum refractive index $n_{surf}=n_0$ at substrate surface 22 and steeply tapers off to an intermediate index $n_i$, while region R2 tapers more gradually from the intermediate index down to the substrate (bulk) refractive index $n_s$.

Usually in Li glasses, in the case of transverse magnetic (TM) waves, the indices $n_t$ and $n_s$ are about the same, while for TE waves $n_t$ is lower than $n_s$ because compressive stress at the knee lowers the TE refractive index relative to the TM one. The portion of the refractive index profiles $n^{TM}(z)$ and $n^{TE}(z)$ for region R1 represents the spike PS in the refractive index having a depth $DOL_{sp}$=DOL=D2. In an example, the intermediate index $n_t$ can be very close to the substrate refractive index $n_s$, as shown in FIG. 2A by way of example.

Example Prism Coupling Apparatus and Mode Spectrum

Example prism-coupling systems suitable for use for carrying out the methods disclosed herein are also described in U.S. Patent Application Publications No. 2014/0368808 and 2015/0066393, which are incorporated by reference herein.

FIG. 3A is a schematic diagram of an example prism-coupling system 28 that can be used to carry out aspects of the methods disclosed herein. The prism coupling methods using the prism-coupling system 28 are non-destructive. This feature is particularly useful for measuring frangible IOX articles 10 for research and development purposes and for QC in manufacturing.

The prism-coupling system 28 includes a support stage 30 configured to operably support the IOX article 10. The prism-coupling system 28 also includes a coupling prism 40 that has an input surface 42, a coupling surface 44 and an output surface 46. The coupling prism 40 has a refractive index $n_p > n_0$. The coupling prism 40 is interfaced with the IOX article 10 being measured by bringing coupling-prism coupling surface 44 and the surface 22 into optical contact, thereby defining an interface 50 that in an example can include an interfacing (or index-matching) fluid 52 having a thickness TH. In an example, the prism-coupling system 28 includes an interfacing fluid supply 53 fluidly connected to the interface 50 to supply the interfacing fluid 52 to the interface. This configuration also allows for different interfacing fluids 52 with different refractive indices to be deployed. Thus, in an example, the refractive index of the interfacing fluid 52 can be changed by operation of the interfacing fluid supply 53 to add a higher-index or lower-index interfacing fluid. In an example, the interfacing fluid supply 53 is operably connected to and controlled by a controller 150.

In an exemplary measurement, a vacuum system 56 pneumatically connected to the interface 50 can be used to control the thickness TH by changing the amount of vacuum at the interface. In an example, the vacuum system is operably connected to and controlled by the controller 150.

The prism-coupling system 28 includes input and output optical axes A1 and A2 that respectively pass through the input and output surfaces 42 and 46 of the coupling prism 40 to generally converge at the interface 50 after accounting for refraction at the prism/air interfaces. The prism-coupling system 28 includes, in order along the input optical axis A1, a light source 60 that emits measuring light 62 of wavelength λ, an optional optical filter 66 that may be alternatively included in the detector path on axis A2, an optional light-scattering element 70 that forms scattered light 62S, and an optional focusing optical system 80 that forms focused (measuring) light 62F, as explained below. Thus, in an example of the prism-coupling system 28, there are no optical elements between light source 60 and prism input surface 42. The components from the light source 60 to the focusing optical system 80 constitute an illumination system 82.

The prism-coupling system 28 also includes, in order along the output optical axis A2 from the coupling prism 40, a collection optical system 90 having a focal plane 92 and a focal length f and that receives reflected light 62R as explained below, a TM/TE polarizer 100, and a photodetector system 130.

The input optical axis A1 defines the center of an input optical path OP1 between the light source 60 and the coupling surface 44. The input optical axis A1 also defines a coupling angle θ with respect to the surface 12 of the IOX article 10 being measured.

The output optical axis A2 defines the center of an output optical path OP2 between the coupling surface 44 and the photodetector system 130. Note that the input and output optical axes A1 and A2 may be bent at the input and output surfaces 42 and 46, respectively, due to refraction. They may also be broken into sub-paths by inserting minors (not shown) into the input and output optical paths OP1 and/or OP2.

In an example, the photodetector system 130 includes a detector (camera) 110 and a frame grabber 120. In other embodiments discussed below, the photodetector system 130 includes a CMOS or CCD camera. FIG. 3B is a close-up elevated view of the TM/TE polarizer 100 and the detector 110 of the photodetector system 130. In an example, the TM/TE polarizer includes a TM section 100TM and a TE section 100TE. The photodetector system 130 includes a photosensitive surface 112.

The photosensitive surface 112 resides in the focal plane 92 of the collecting optical system 90, with the photosensitive surface being generally perpendicular to the output optical axis A2. This serves to convert the angular distribution of the reflected light 62R exiting the coupling prism output surface 46 to a transverse spatial distribution of light at the sensor plane of the camera 110. In an example embodiment, the photosensitive surface 112 comprises pixels, i.e., the detector 110 is a digital detector, e.g., a digital camera. In an example, each pixel can have a dimension of between 4 microns and 5 microns, e.g., 4.65 microns Splitting the photosensitive surface 112 into TE and TM sections 112TE and 112TM as shown in FIG. 3B allows for the simultaneous recording of digital images of the angular reflection spectrum (mode spectrum) 250, which includes the individual TE and TM mode spectra 250TE and 250TM for the TE and TM polarizations of the reflected light 62R. This simultaneous detection eliminates a source of measurement noise that could arise from making the TE and TM measurements at different times, given that system parameters can drift with time.

FIG. 3C is a schematic representation of a mode spectrum 250 as captured by the photodetector system 130. The mode spectrum 250 has total-internal-reflection (TIR) section 252 associated with guided modes 252TE and 252TM and a non-TIR section 54 associated with radiation modes and leaky modes 254TE and 254TM. The transition between the TIR section 52 and the non-TIR section 54 defines a critical angle for each of the TE and TM polarizations and is referred to as the TIR-PR transition. The location of the TIR-PR transition for each polarization is referred to as the TIR-PR location.

The mode spectrum 250 includes both a TM mode spectrum 250TM and a TE mode spectrum 250TM. The TM mode spectrum 250TM includes mode lines or fringes 252TM while the TE mode spectrum 250TE includes mode lines or fringes 252TE. The mode lines or fringes 252TM and 252TE can either be bright lines or dark lines, depending on the configuration of the prism-coupling system 28. In FIG. 3C, the mode lines or fringes 252TM and 252TE are shown as dark lines for ease of illustration. In the discussion below, the term "fringes" is also used as short-hand for the more formal term "mode lines."

The stress characteristics can be calculated based on the difference in positions of the TM and TE fringes 252TM and 252TE in the mode spectrum 250. At least two fringes 252TM for the TM mode spectrum 250TM and at least two fringes 252TE for the TE mode spectrum 250TE are needed to calculate the surface stress CS. Additional fringes are needed to calculate the stress profile CS(x), including the knee stress CSk.

With reference again to FIG. 3A, the prism-coupling system 28 includes a controller 150, which is configured to control the operation of the prism-coupling system. The controller 150 is also configured to receive and process from the photodetector system 130 image signals SI representative of captured (detected) TE and TM mode spectra images. The controller 150 includes a processor 152 and a memory unit ("memory") 154. The controller 150 may control the activation and operation of the light source 60 via a light-source control signal SL, and receives and processes image signals SI from the photodetector system 130 (e.g., from the frame grabber 120, as shown). The controller 150 is programmable to perform the functions described herein, including the operation of the prism-coupling system 28 and the aforementioned signal processing of the image signals SI to arrive at a measurement of one or more of the aforementioned stress characteristics of the IOX article 10.

FIG. 3D is another schematic representation of an example measured mode spectrum 250 of an IOX article 10 formed using a Li-containing glass substrate 20 and an ion-exchange process using a mixture of $NaNO_3$ and $KNO_3$, with the mode spectrum including TM and TE spectra 250TM and 250TE (upper and lower portions, respectively) with respective mode lines 252TM and 252TE. The TIR-PR transition is denoted for the TM mode specrum 250TM. The Li-containing glass was 196HLS having a fictive temperature of 638° C. The glass was subjected to a Li+⇔K+, Na+ ion-exchange process by placing the glass sample in a bath having 60 wt % $KNO_3$ and 40 wt % $NaNO_3$ at 390° C. for 3 hours.

As is known in the art, the fringes or mode lines 252TM and 252TE in the mode spectrum can be used to calculate surface compression or "compressive stress" CS and depth of layer DOL associated with an ion-exchange layer that forms an optical waveguide. In the present example, the mode spectrum 250 was obtained using a commercially available prism-coupling system, namely the FSM6000L surface stress meter ("FSM system"), available from Luceo Co., Ltd. of Tokyo, Japan, which system is similar to the one described herein.

The measured values of CS and DOL for the example IOX article 10 were 575 MPa and 4.5 microns, respectively. These are the parameters of the K+ enriched layer or spike region R1 adjacent the IOX article surface 22. The auxiliary vertical dashed lines on the left-hand side of the TE and TM mode spectra 250TE and 250TM were added to FIG. 3D and show positions in the spectra in which the aforementioned conventional FSM system assigns to correspond to the surface indices $n_{surf}^{TM}$ and $n_{surf}^{TE}$. The difference in these positions is proportional to the surface stress or compressive stress CS. These positions are also used in the calculation of the depth of layer or DOL.

In the mode spectrum 250 for a chemically strengthened Li-containing glass having undergone a Li+⇔K+, Na+ ion exchange, the position of the transition from the bright to the dark portion of the spectrum (i.e., the TIR-PR location) observed after the last fringe 52 in the spectrum that corresponds to the highest-order guided mode, is shifted in the TE spectrum 250TE as compared to the TM spectrum 250M. These TIR-PR locations for the TM and TE polarizations correspond to the effective indices at the knee KN, which are respectively denoted in FIG. 3D as $n_{knee}^{TM}$ and $n_{knee}^{TE}$ respectively. The effective indices at the surface are denoted $n_{surf}^{TM}$ and $n_{surf}^{TE}$ for the TM and TE polarizations and are shown for reference (see also FIGS. 2A and 2B).

This shift in the location of the TIR-PR location (i.e., the location of $n_{knee}^{TM}$ and $n_{knee}^{TE}$) between the TE and TM spectra is proportional to the knee (compressive) stress CSk, i.e., the compressive stress CS at the knee KN, i.e., the depth at which the K+ concentration in spike region R1 decreases approximately to the constant-level concentration originally in the substrate (e.g., the spatially constant concentration in the glass matrix that makes up substrate body 21).

In the idealized mode spectra 250 of FIG. 3D, the TIR-PR transitions are shown as being infinitely sharp. With reference to the schematic diagram of an example TM mode spectrum 250TM of FIG. 3E, in practice, the TIR-PR locations are defined by a gradual transition from light to dark, with each transition having an intensity slope SLP, a width $W_{TIR-PR}$ and a location $x'_{TIR-PR}$, each of which can vary due to experimental factors and imperfections in the measurement system. For example, with reference to FIGS. 3F and 3G, when a leaky mode 254L falls very close to the TIR-PR transition, it can affect the intensity distribution at the TIR-PR location so that the TIR-PR location $x'_{TIR-PR}$ is shifted by an amount $\Delta x'$ from its original location to a shifted location $xs'_{TIR-PR}$, wherein the local coordinate x' is shown. Note that the width $W_{TIR-PR}$ can also be affected and is typically increased.

Mitigation of the main factors that adversely affect the accurate determination of the TIR-PR transitions for the TM and TE polarizations to improve the measurement of the knee stress CSk are discussed below.

The measurements of the mode spectrum 250 of an IOX article 10 having an IOX region 24 defined by the K+ penetration of the IOX process, along with the TIR-PR locations for the TM and TE mode spectra 250TM and 250TE, can be combined and used for effective QC of a family of stress profiles that provide superior resistance to fracture. The spike region R1 is relatively small in thickness when compared to the substrate thickness T. For example, the spike region R1 may be 10 microns deep (i.e., $DOL_{sp}$=10 microns), while the substrate may be T=800 microns thick. The profile of the spike SP may have a shape similar to a complementary error function (erfc) shape, but may also be similar to a linear depth distribution, Gaussian depth distribution, or another distribution. The main features of the spike SP are that it is a relatively shallow distribution and provides a substantial increase in the surface compression over the level of compression at the bottom of the spike as defined by $DOL_{sp}$.

Figure 4:
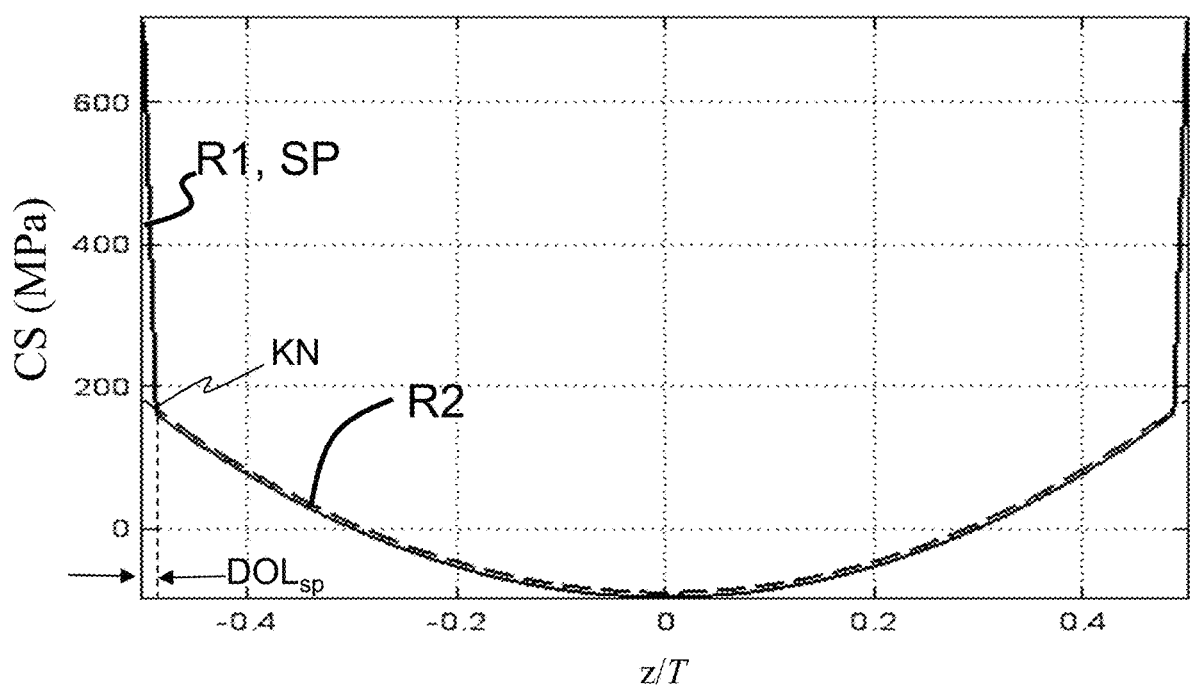
FIG. 4 is a plot of the stress (MPa) versus a normalized position coordinate z/T, showing the model stress profile (solid line) for a sample chemically strengthened Li-containing glass that has undergone a K+ and Na+ ion exchange, wherein the dashed line represents the model profile for Na+ diffusion only, noting that the model profile has ion exchange taking place at two surfaces that respectively reside at z/T=−0.5 and +0.5.

FIG. 4 is an example plot of the compressive stress CS (MPa) versus a normalized position coordinate z/T, showing the model stress profile (solid) for an example chemically strengthened Li-containing glass substrate 20 that has undergone a K+ and Na+ IOX process. In the plot of FIG. 4, the dashed line represents the model profile for Na+ diffusion only (note that the model profile has the IOX process taking place at two surfaces that respectively reside at z/T=−0.5 and +0.5). The example profile has a parabolic deep portion or region R2 and the surface spike region R1 with spike SP.

In the present disclosure, the assumed convention is that compressive stress CS is positive and that tensile stress is negative. The model profile of FIG. 4 has a linear spike SP in region R1 added on top of a deep quadratic profile in region R2. Another feature of the spike SP is also recognized from FIG. 4, namely that the typical slope of the stress distribution in the spike R1 is significantly higher than the typical slope in the deep portion R2 of the profile, which is assumed to follow a power law, which in this specific example is parabolic (with power p=2), for the purposes of making QC measurements.

Figure 5A:
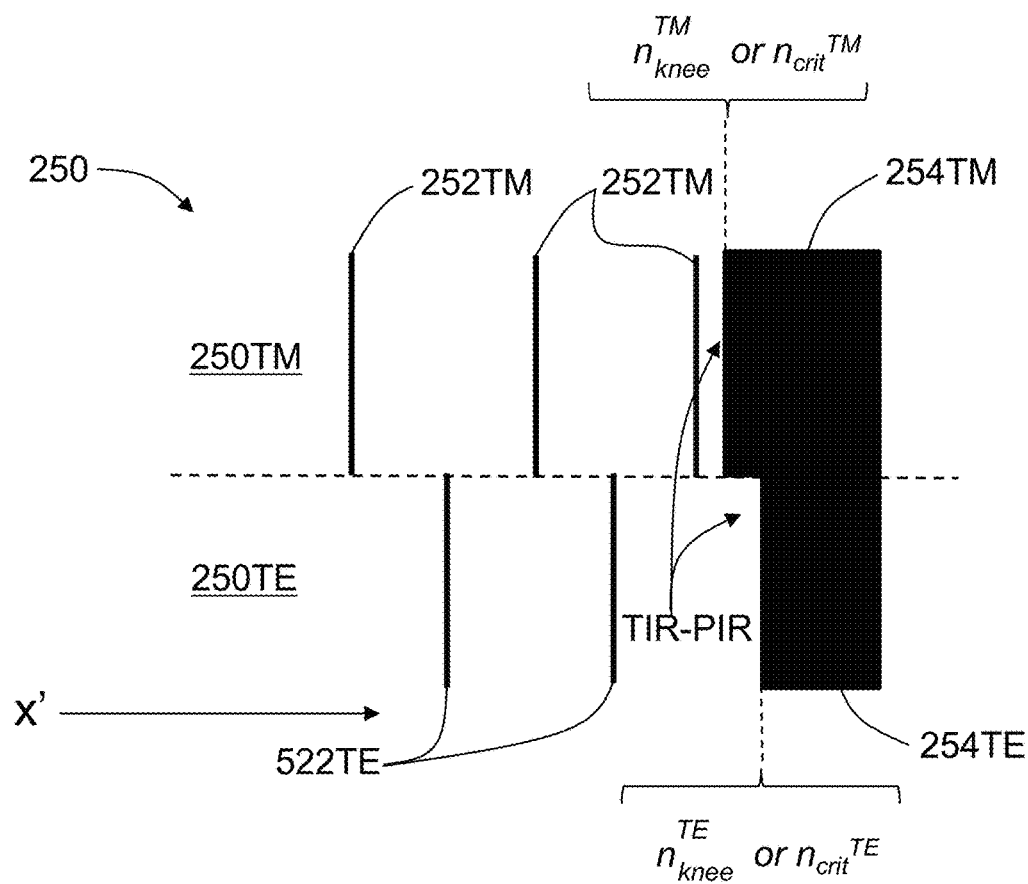
FIG. 5A is a schematic representation of a measured mode spectrum showing the TE and TM mode spectra for an example chemically strengthened Li-containing glass sample.

FIG. 5A is a schematic representation of a measured mode spectrum 250 showing the TE and TM mode spectra 250TE and 250TM based on actual measured mode spectra for an example chemically strengthened Li-containing IOX article 10. Note again the offset in the x' direction of the dark regions 254TM and 254TE. The TIR-PR locations for the TE and TM spectra are also shown and are offset relative to each other.

Assessing and Limiting the Adverse Effects of Sample Warpage

It has been found that non-flatness (warpage) of an IOX article 10 can significantly degrade the precision of the CSk measurement by introducing random and systematic quasi-random errors in the detected location of the TIR-PR transitions. This is particularly problematic because the amount of warpage that can adversely affect the knee stress measurement is not readily observable by the human eye. Thus, an aspect of the disclosure is a method for ensuring that an accurate determination of the knee stress can be made on a given glass sample that could have an amount of (unseen) warp.

Figure 5B:
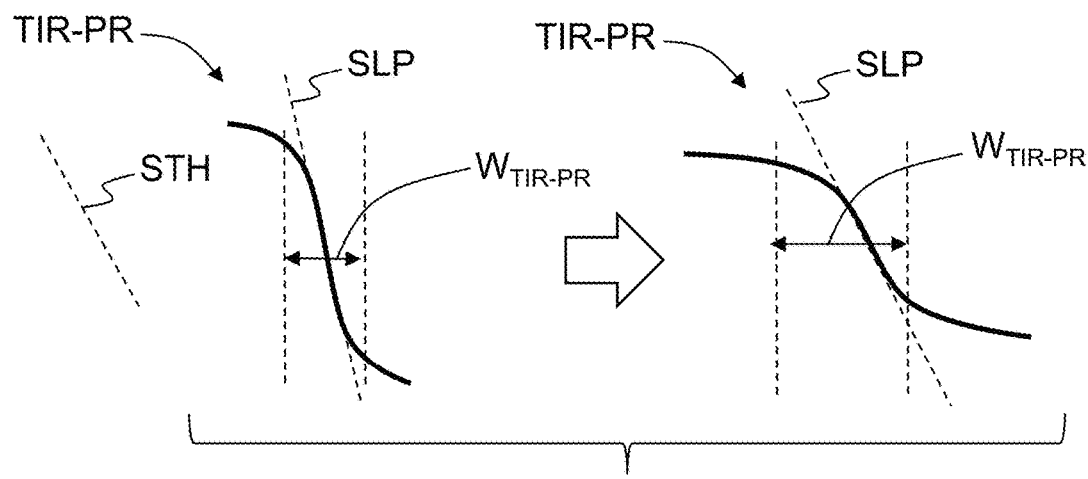
FIG. 5B is a schematic diagram of the TIR-PR transition illustrating how the slope of the TIR-PR transition in the measured mode spectrum changes due to a warped IOX article.

FIG. 5B is a schematic diagram that shows on the left side the TIR-PR transition for a flat IOX article 10 and on the right side the TIR-PR transition for a warped IOX article. A slope SLP of the TIR-PR transition is denoted by the slanted dashed line. Note that the warpage makes the TIR-PR transition less steep and more blurry (as indicated schematically by the reduced contrast), which results in increased uncertainty for the position of the maximum slope of the transition, which is normally assigned as the TIR-PR position.

Furthermore, it has been observed that warpage of the IOX article 10 can make the intensity pattern of a leaky mode in the mode spectrum 250 appear similar to the pattern of a guided mode, and vice versa, depending on the degree and orientation of the warp (convex or concave), and also depending on the position of the apex of the warped (e.g., curved) glass surface relative to the center of the prism coupling area, and more specifically to the illuminated region of the coupling surface 44 of the coupling prism 40. These effects lead to relatively large errors in detecting the TIR-PR location, which can lead to corresponding errors in measurement of the knee stress CSk on the order of tens of MPa.

An aspect of the methods disclosed herein tests for signatures of warp in the measured mode spectra 250. Signatures of warp include for example a significantly smaller (less steep) slope of the light intensity for the TIR-PR transition than is typical for flat samples, as illustrated in FIG. 5B. Another signature is a wider than expected spread in the TIR-PR transition, as indicated by the increased breadth of the curve formed by the derivative of the intensity profile (i.e., the derivative of the angular distribution of intensity).

The tests for whether the level of warpage is acceptable may be performed using measurements of the TIR-PR transition location for one of the TM and TE mode spectra, or both the TM and the TE mode spectra. In the usual measurements of stress using the mode spectrum 250, the TM transition is naturally sharper, especially for chemically-strengthened Li-containing glasses. As such, the tests for whether the level of warpage in the sample is acceptable may be preferably restricted to the TIR-PR transition of the TM mode spectrum only.

It has been observed that a warped IOX article 10 also tends to broaden the mode fringes 252TM and 252TE in the corresponding mode spectra 250TM and 250TE that correspond to guided or quasi-guided optical modes, especially with respect to the narrowest of these mode fringes. A corollary of this broadening is also a reduction in the contrast of these fringes. Hence, to limit random and quasi-random errors resulting in part from sample warpage, the method utilizes measurements of the breadth of selected narrowest fringes, or the peak slope of the derivative of the intensity profile across such fringes (e.g., the peak absolute value of the second derivative), the fringe contrast, or any combination thereof, and comparisons of the measured values to expected acceptable standards based on modeling or previous measurements of samples with acceptable levels of warp.

In an example, any combination of the breadth, peak second derivative, and contrast of the intensity profile of the guided-mode TM fringe having the closest effective index to that of the TM critical angle, and higher effective index than that of the TM critical angle, can be used for testing whether the amount of warp in the sample is acceptable, i.e., that leads to a measurement of CSk having adequate accuracy.

Note that in some embodiments, the selected mode fringe for this test may be simply the narrowest fringe in the given mode spectrum without regard for where it is relative to the critical angle (i.e., the TIR-PR transition location) as even a crude estimate of the TIR-PR location may be postponed for after the test which assesses whether the amount of warpage is acceptable.

In an example, the method conditions the mode spectra (signal) by standard de-noising techniques, employing for example a LOESS algorithm and/or digital low-pass or band-pass filtering. The LOESS algorithm is described in the article by W. S. Cleveland, "Robust locally weighted regression and smoothing scatterplots", Journal of the American statistical association, vol. 74, No. 368, pages 829-836 (December 1979). De-noising of the signal is very helpful for reducing errors in the decision routines caused by noise-induced large excursions of the derivatives of the signal. The bandwidth of the low-pass filter or band-pass filter is chosen such that filter-induced broadening of the narrowest fringes in the spectra is appropriately smaller than the threshold for rejecting a spectrum that is unacceptably broadened by warp.

Thus, an aspect of the disclosure includes a method of improving a measurement of knee stress in a chemically strengthened Li-containing glass sample (IOX article 10) having a warped surface and a body and that includes an IOX region that defines a stress profile having a knee. The method comprises: capturing an image of at least one of a TE mode spectrum and a TM mode spectrum; measuring a slope of light intensity at a transition between total-internal reflection and partial-internal reflection (TIR-PR) and measuring a width of the TIR-PR transition for at least one of the TE mode spectrum and TM mode spectrum; and comparing the measured slope SLP and the measured width $W_{TIR-PR}$ to a slope (steepness) threshold STH and a width threshold $WT_{TIR-PR}$ associated with reference glass sample having a flat surface.

In an example reference glass sample is formed using the same IOX process used to form the warned glass sample.

In another example, the method includes: measuring a fringe width of one of the narrowest TE mode fringe and the narrowest TM mode fringe; and comparing the measured fringe width to a fringe width threshold as defined by the reference glass sample, and only proceeding with the determining of the knee stress if the measured fringe width is as wide or smaller than the fringe width threshold.

Assessing and Limiting Adverse Effects of Illumination Non-Uniformities

Another imperfection that causes systematic and quasi-random errors in the mode spectra relates to non-uniformities in the illumination used to generate the mode spectra. An example of such illumination non-uniformity is a gradient in the angular illumination spectrum, and a changing orientation of the illuminating angular spectral distribution relative to the mode spectra.

A significant gradient of the angular spectrum of the intensity distribution can be produced by the combination of the light source 60, the coupling prism 40, and surrounding apertures of the prism coupling system used to capture images of the mode spectra. Illumination non-uniformities are particularly problematic when they are in the vicinity of the TIR-PR transition location and when there is an intensity gradient along the x' direction as shown in FIGS. 3C, 3D and 5A for example. This is because illumination non-uniformities can shift the TIR-PR transition location and fringe locations, and can result in an error in the direct CSk measurement when the shifts are not the same for the TE and TM mode spectra. Another type of non-uniformity is contamination of the detector array, which could result local darkening of some pixels and interfere with the detection of the steepest intensity slope for determining the critical angle location.

Even if the gradient of illumination is the same in the vicinity of the TE and TM TIR-PR transition locations, the corresponding apparent shifts of the critical angle can be different because slope of the TIR-PR transition is different for the TE and the TM mode so that their sensitivity to an illumination gradient is different.

An aspect of the disclosure is directed to methods of improving the CSk measurement by reducing the errors caused by illumination non-uniformities. In one example, a low-pass-filtered component of the signal in the bright part of the reflected angular spectrum (the TIR region) is analyzed and if it contains gradients greater than an acceptable upper limit, the controller 150 (via software) requires that the illumination gradients be fixed before taking measurements. This can be done by adjusting the light source 60 or by adding an optical gradient filter 66 in the light beam 62 from the light source 60.

Assessing and Mitigating the Adverse Effects of Leaky Modes

With reference again to FIGS. 3E through 3G, it has been recognized that the presence of a leaky mode (254L) in close proximity to the TIR-PR transition location causes the intensity profile in the vicinity of the transition to change significantly. This in turn can lead to significant systematic errors, as well as quasi-random errors. Such errors can combine with errors from other effects like moderate warp of the samples or gradients in the illumination intensity, as discussed above. That said, the leaky mode issue by itself can be quite problematic because it can shift the TIR-PR transition location (by Δx' in FIG. 3G) and lead to errors in the estimate of CSk that can be many tens of MPa, which is unacceptably large.

A leaky mode has an effective index that is lower than the lowest index in the waveguide region (i.e., TIR section 252), which in our example, is lower than the refractive index at the bottom of the potassium spike (e.g., than the refractive index corresponding to the knee-point in the profile). In this case, the light captured in this mode inside the waveguide experiences some bouncing in the waveguide region (IOX region 24) before leaking into the underlying portion of the body 21 of the glass substrate 20

Figure 3F:
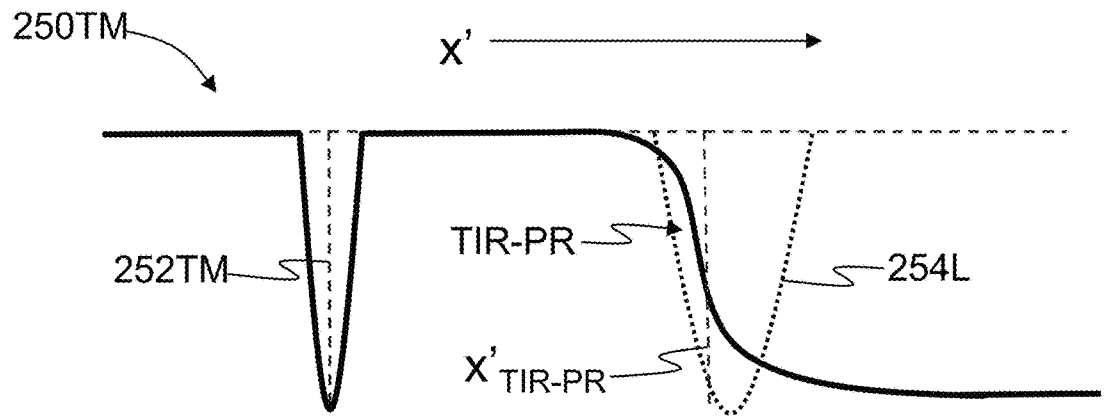
Figure 3G:
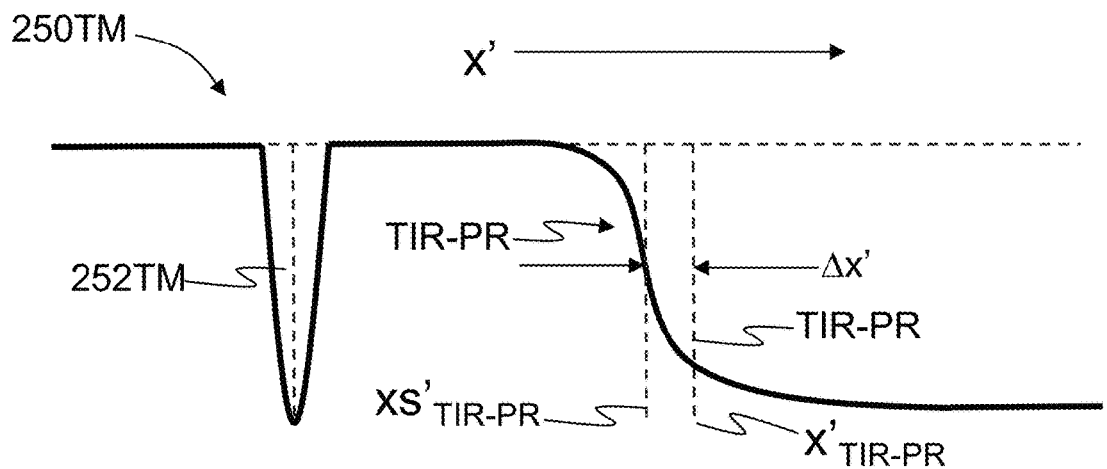

A leaky mode 254L with an effective index close to the index of the TIR-PR transition tends to produce a coupling resonance in the vicinity of this transition and thus deforms the angular intensity distribution around the TIR-PR transition location, as illustrated in FIGS. 3F and 3G. This in turn causes a shift Δx' in the location of the maximum slope of the intensity distribution at the TIR-PR location relative to the true location associated with the critical angle. That is to say, a leaky mode 254L can cause a shift in the measured TIR-PR transition location relative to its actual location measured in the absence of the leaky mode.

An aspect of the disclosure is directed to improving the measurement of the knee stress CSk by accounting for (i.e., compensating for) the shift in the TIR-PR transition location due to a leaky mode 254L.

If the TIR-PR transition location can be established as usual, but there is a broad resonance in the intensity distribution at a position corresponding to a lower effective index than the TIR-PR transition, then a correction for the shift in the position of the highest-slope is perform. The correction is calculated based on the distance between the location of the intensity extremum corresponding to the broad resonance of the leaky mode and the measured raw position of the peak slope of the TIR-PR transition. This distance may be normalized to the distance between two highest-order modes in the same polarization state (TM or TE) for which the position of the transition is currently evaluated, or any combination of spacings of the guided modes in effective index, or corresponding positions of their coupling resonances in angular space or on the measurement detector.

With a slow continuous increase in the depth D1 of the potassium ions in region R1 of the profile (see FIG. 2), the effective index of the leaky mode slowly increases, getting closer and closer to the effective index of the TIR-PR transition. At the same time, the breadth of the corresponding resonance in the mode spectra decreases, and the contrast of the corresponding spectral feature (mode fringe) increases. In the case when the angular distribution of the light reflected from the prism-sample interface 50 is being detected and analyzed (i.e., in the form of a mode spectrum 250), the photodetector system 130 may be configured to collect reflected light 62R in a region where the mode fringes corresponding to coupling resonances of guided modes are dark fringes. The resonance corresponding to the leaky mode is then also dark, and its increased contrast upon approaching the TIR-PR transition location also results in further lower light intensity (darker resonance).

Figure 5C:
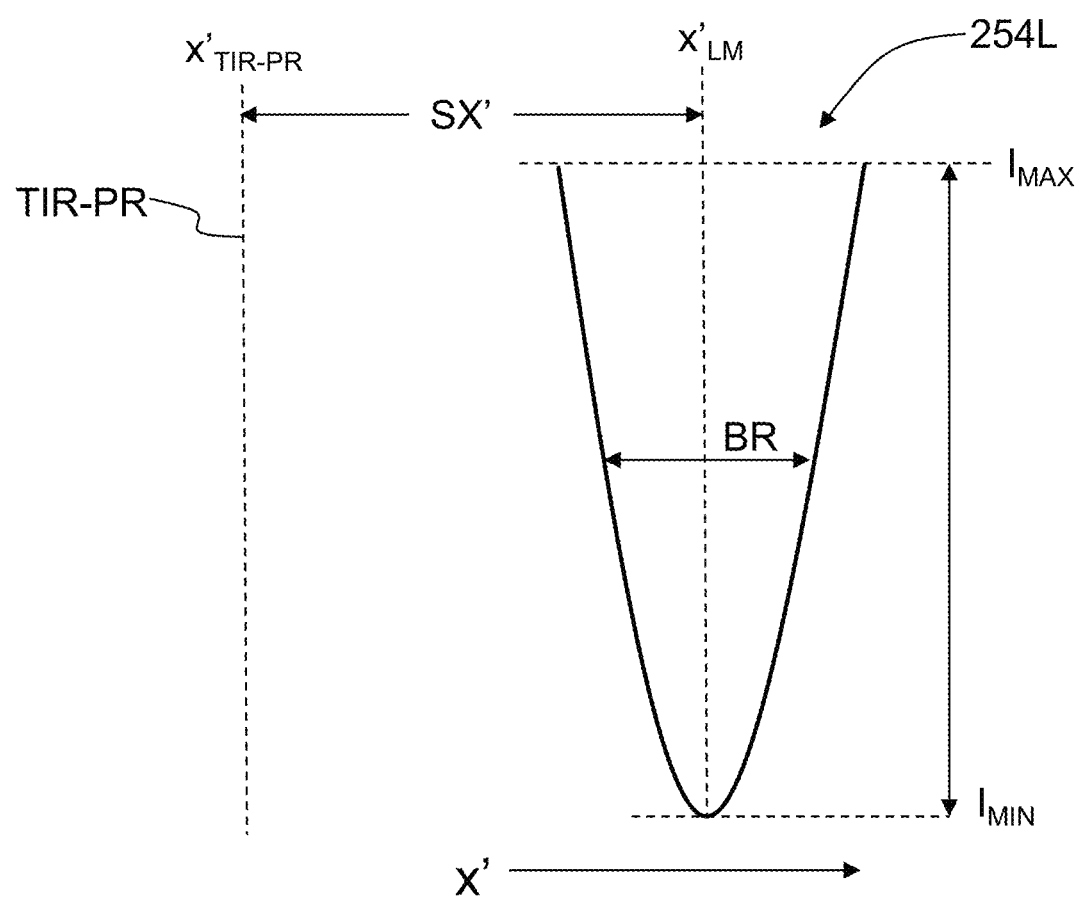
FIG. 5C is a schematic diagram of an example leaky mode resonance illustrating example measurement parameters used in correcting for a shift in the TIR-PR transition location.

FIG. 5C is a schematic diagram of an example leaky mode resonance, i.e., intensity distribution of the leaky mode. In an embodiment, a correction for the shift in the measured position of the critical angle (TIR-PR location) is calculated based a combination comprising measured values of the breadth BR of the resonance of the leaky mode (e.g., full-width half maximum), a contrast of the resonance (intensity distribution) of the leaky mode based on $I_{MAX}$ and $I_{MIN}$ intensities (e.g., (e.g., Contrast=$[I_{MAX}-I_{MIN}]/[I_{MAX}+I_{MIN}]$), a normalized intensity at the intensity extremum of the leaky mode based on the $I_{MAX}$ and $I_{MAIN}$ intensities and spacing SX' (in effective index, or a corresponding variable such as angular spacing, pixel spacing, or distance on the detector) between the location $x'_{LM}$ of the detected extremum of the leaky mode and the raw position $x'_{TIR-PR}$ of the TIR-PR transition peak slope. In some embodiments, the ratio of normalized intensity on the two sides of the leaky-mode resonance is also used to calculate the correction.

Thus, an aspect of the methods disclosed herein includes a method of correcting the shift of the TIR-PR location in either the TM mode spectrum 250TM or both TM and TE mode spectra 250TM and 250TE due to the presence of one or more nearby leaky modes 254L (TE, TM). This correction extends the range of profiles over which knee stress measurements can be made, i.e., it broadens the measurement window for which the knee stress CSk can be determined.

The TM and TE measurement sweet spots can be measured as a fractional part of the mode spacing, and in an example are normally each about 0.5 modes wide. Since the TM and TE measurement sweet spots are offset relative to each other, the total measurement window is actually narrower, e.g., about 0.3 modes wide when considering both TM and TE mode spectra 250TM and 250TE.

With the correction made for the presence of a leaky move, the measurement window for each of the TM and TE spectra can be about 0.9 modes wide. If there is 0.2 mode shift between TM and TE spectra 250TM and 250TE, then the overall measurement window is 0.7 modes wide, which represents a greater than 2× increase in the measurement window.

An example method of compensating for the presence of a leaky mode in the calculation of the knee stress CSk is as follows:

1) Determine the position of maximum slope of the TIR-PR transition for each of the TM and TE mode spectra.
2) Determine the leaky mode position from the TE and TM mode spectra where the leaky mode is defined as a relative minimum after the TIR-PR transition. In a specific example, the relative minima are defined as normalized intensity minima of 6/255 (absolute units), occurring within 30 pixels.
3) Determine the TM and/or TE leaky mode correction amount in either number-of-pixels, effective index, or angular space.
4) Determine the leaky mode width at half max.
5) Suppress the leaky mode correction if the leaky mode correction is a greater distance than leaky mode offset.
6) Determine the final position of critical angle as the initial maximum slope position+the leaky mode correction.
7) Correct for cases when the leaky mode is exactly at the critical angle by shifting the critical angle to lower effective index.
8) Correct for cases where TE has higher total mode count than TM. This is caused by TE transition broadening due to warp.

Another aspect of the disclosure is directed to a method of improving a measurement of knee stress in a chemically strengthened Li-containing glass sample having a surface and a body and that includes a stress profile having a knee and that defines a waveguide that supports light as guided waves and a leaky mode. The method comprises: capturing an image of a TE mode spectrum and a TM mode spectrum of the guide waves and leaky mode; measuring a position of maximum slope of a transition between a total-internal reflection and a partial-internal reflection (TIR-PR) for the light supported in the waveguide for each of the TE mode spectrum and the TM mode spectrum; determining from the TE and TM mode spectra a position of the leaky mode as a relative minima after the TIR-PR transition; determining from the leaky mode position an amount of shift in the TIR-PR position caused by the leaky mode; adding the amount of shift from the measured position of the TIR-PR transition to arrive at a corrected TIR-PR transition location; and using the corrected TIR-PR transition location to determine the knee stress.

Other Approaches to Increasing the Size of the Measurement Window

The systems and methods described so far have allowed effectively to increase the size of the measurement window or "sweet spot" for measuring the knee stress CSk of an IOX article 10 by calculating corrections for the shift in the critical angle when the fractional part of the non-integer mode number ("fractional mode number") of the spike in the polarization state under consideration (i.e., TE or TM) is greater than about 0.65 and smaller than 1. As is known for direct measurement of the knee stress CSk, the direct measurement of the TIR-PR transition is relatively precise when the fractional mode number is between about 0.2 and 0.7, and more preferably is between about 0.3 and 0.65.

Another aspect of the disclosure is directed to methods that correct for a shift in the TIR-PR transition location measured from the location of the peak slope of the transition when the distance from the last guided mode to the peak-slope location corresponds to a fractional mode number of between 0 and 0.2. In this case, the contribution to the shift in the peak-slope location due to a leaky mode is not significant since the closest leaky mode is quite far from the TIR-PR transition location. The shift in the peak-slope location relative to the actual TIR-PR transition location in this case is caused by the broadening of the resonance of the highest-order guided mode. This broadening is caused by the limited resolution of the measurement system, the strength of coupling of the guided mode to the modes of propagation in the prism, as well broadening due to (accepted) levels of warp in the measured IOX article, as discussed above.

The broadening of the resonance of the highest-order guided mode causes the intensity distribution of the coupling resonance to overlap on one side with the TIR-PR transition. This in turn causes the intensity distribution of the resonance to be asymmetric and also causes a change in shape in the intensity distribution in the vicinity of the TIR-PR transition, similar to what happens when a leaky mode is present. This can cause the location of highest slope of the TIR-PR transition, which is used as a surrogate for the location of the critical angle, to shift as a result of the change in angular intensity distribution in the close proximity of the TIR-PR transition. The amount of necessary correction can be determined by analyzing a large number of different spectra.

In one embodiment, the correction for the shift caused by the proximity of a leaky mode, and the correction for the shift caused by a close proximity of a guided mode to the TIR-PR transition, are combined into a single correction with a single mathematical expression or logical and mathematical expression, even though two separate causes for the shift exist that normally don't operate simultaneously since only one or the other usually causes a shift.

In the above embodiments, the signature of a leaky mode in the measured coupling spectrum is substantially different from that of a guided mode, and a relatively straightforward method for detecting and distinguishing leaky modes from guided modes was implemented. In particular, the resonance for the leaky mode in this case is much broader than that of nearby guided mode, and the contrast of the intensity profile of the leaky mode is much smaller than that of the guided modes.

In some cases the distance between a mode, guided or leaky, and the critical angle is very small, less than about 0.15 of typical mode spacing of the spike. In such cases it becomes much more difficult to distinguish between a guided mode and leaky mode based on only one or two parameters, such as breadth of the resonance and contrast of the resonance, as both these parameters have overlap in their corresponding ranges observed for leaky and guided modes that are close to the critical angle.

Furthermore, a guided mode may have enough broadening to have its intensity on the lower-index side of the angular intensity distribution lowered significantly, making its intensity distribution very similar to that of a leaky mode in the vicinity of the TIR-PR location. Then it may not be clear whether the critical angle should be assigned to the steepest slope on the high-index side of the resonance or on the low-index side of the resonance, as it is not known whether the resonance belongs to a guided or leaky mode.

Furthermore, even when it is possible for a human to identify a feature in the intensity pattern that can help assign the resonance as leaky or guided, effects of warp and imperfect illumination can easily cause errors in the assignment of such a questionable resonance as leaky or guided. In this case, a more sophisticated approach is preferred for assigning a resonance as leaky or guided when the location of the TIR-PR transition is within the range of substantial effect of a nearby resonance.

The assignment of a resonance as guided or leaky utilizes the breadth of the resonance, the contrast of the resonance, the difference in intensity distribution on either side of the resonance, the peak second derivative in the resonance intensity profile, the breadth of the nearest TE or TM guided-mode resonance, the contrast of the nearest TE or TM guided-mode resonance, and the relative spacings of all resonances, including all guided-mode resonances having higher effective index higher than the questionable resonance, and the spacing from the already identified highest-order-mode resonance and the questionable resonance.

An example method uses the breadth of the resonance and the contrast of the resonance to identify and assign a resonance as "leaky" after the TIR-PR transition. The leaky mode position is determined from TE and TM mode spectra where the leaky mode is defined as a relative minimum after the TIR-PR transition. In a specific example, the relative minima are defined as normalized intensity minima of 6/255 (abs units), occurring within 30 pixels.

Further, the example method can employ empirical additive corrections to shift the TIR-PR transition to account for leaky mode presence. In an example, LW is defined as the leaky mode breadth (FWHM) and LO is defined as the leaky mode position offset (px) from TIR-Pr transition maximum slope. A specific example of leaky mode correction for TM is defined as: TM_Correction=−3.8·LW+61.1·(1/LO). A specific example of leaky mode correction for TE is defined as: TE_Correction=10.6·LW+−31.2·(1/LO). The leaky mode correction is then added to the respective TM or TE TIR-PR transition location of maximum slope.

Improved CSk Measurement by Using High-Quality Mode Spectrum Images

The above-described methods can significantly increase the range of applicability of the direct CSk method by substantially reducing the systematic error when any of the TIR-PR transitions (the TM or the TE) is not strictly inside a measurement sweet spot. The only cases when significant variability in the measurements of a sample occurs is one when a guided mode is located very close to the TIR-PR transition, e.g., within less than about 0.05 mode spacings of the critical angle. In this case, it sometimes happens that the mode resonance contrast is significantly decreased and the mode is not properly detected. Hence, the described new methods can be employed to increase (e.g., double) the range of conditions that can be measured using the direct CSk method.

In an example, the method can account for this near-integer total mode count in the TM spectrum 250TM by shifting the TIR-PR transition toward the lower effective index space. In a specific example, when a TE spectrum contains a leaky mode and the TM spectrum does not appear to contain a leaky mode (due to the above reduced resonance contrast), and TM fractional mode count is between 0.65 to 1.00, the TM TIR-PR transition can be shifted toward lower index space by a select number of pixels, e.g., 8 pixels, as determined empirically by analyzing hundreds of mode spectra.

Despite the improved precision and increased range of applicability of the above-described methods, the achieved precision of a single direct CSk measurement may not be adequate in many cases for performing QC. Hence, another aspect of the present disclosure includes methods of QC that have better precision.

In one embodiment, the quality of the mode spectra image is assessed based on comparing the breadth of the narrowest coupling resonances to expected reference values for assumed high-quality mode spectra images. A measurement is only accepted if the mode spectra image is deemed to pass select criteria that define a high-quality mode spectra image. Further, the mode spectra images are captured at least twice, preferably three times, and the sample position relative to the prism, or the illumination intensity or angular distribution is changed between different measurements, such that several (at least 2) raw values are obtained for the direct CSk and the reported value is the average of the at least two raw values.

An example method includes defining one or more standards for the image quality of the captured mode spectra image(s) so that the knee stress CSk can be determined to within a precision of +/−15 MPa, +/−10 MPa, or even +/−5 MPa. In an example, the method includes accurately measuring the half-max intensity width of the mode fringes. This can include taking into account the overshoot of the intensity on one side of the fringe that may be normalized by the overshoot of intensity on the other side of the fringe, measuring the relative height of TM and TE intensity slope at the transition location (location of maximum slope), and then determining/assigning the TM and TE intensity slope at the transition location (location of maximum slope).

In an example method, the image of the given TM or TE mode spectra 250TM or 250TE is deemed unacceptable for calculating the knee stress CSk if:

1) TE fringe overshoot >16/255 (abs units) AND TM intensity slope >−25/255 (abs units) AND Average fringe width >8 (px)

OR

2) TM intensity slope >−10/255 (abs units) AND Average fringe width >8 (px)

OR

3) TE fringe overshoot >30 (abs units) AND Average fringe width >8 (px)

OR

4) Average fringe width >40 (px)

Another aspect of the disclosure is a method of improving a measurement of a knee stress in a chemically strengthened Li-containing glass sample having a surface and a body and that includes a stress profile having a knee and that defines a waveguide that supports light as guided modes, comprising: capturing an image of a TE mode spectrum and a TM mode spectrum; measuring a slope SLP of a transition between a total-internal reflection and a partial-internal reflection (TIR-PR) for the light supported by the waveguide for each of the TE mode spectrum and the TM mode spectrum; comparing the slope SLP to a steepness threshold STH and using the slope to determine a location of the TIR-PR transition and using the corrected TIR-PR transition location to determine the knee stress only if the slope SLP is greater (steeper) than the select steepness threshold.

Improved Measurement of CSk by Combining Direct and Indirect Methods

A further improvement in the precision in the measurement of the knee stress CSk is obtained by another embodiment of the present invention, where the accuracy of a well-implemented direct-CSk method is combined with the high precision of an indirect method such as the "birefringence of the higher-order guided mode method" or BHOGM.

The direct CSk method uses the birefringence as determined from the offset between the TM and TE TIR-PR transition locations (see e.g., FIG. 3D) and the stress optic coefficient SOC for the material, e.g., via the relationship $CSk=[n_{crit}^{TE}-n_{crit}^{TM}]/SOC$, where $n_{crit}^{TE}$ and $n_{crit}^{TM}$ are the values of the effective index at the critical angle, i.e., at the TIR-PR transitions for the TE and TM mode spectra 250TE and 250TM respectively.

As noted above, this method is improved to increase the measurement accuracy and precision of the knee stress CSk by reducing non-uniformities in the illumination, accounting for the presence of leaky modes and their effect on the TIR-PR transition shape to correct the intensity profile of the TIR-PR transition for shifts in the location of maximum slope.

The improved method utilizes several image characteristics of the mode spectra 250 to correct the TIR-PR maximum slope location, which results in a much more precise calculation of the direct CSk. The mode spectra image characteristics of interest include: the TIR transition width at half maximum of the 1st derivative; the TIR-PR transition negative slope value at the minima; the intensity after transition, intensity at the transition, intensity before transition, slope overshoot before and after the transition; the offset of the TIR-PR transition due to leaky modes; the leaky mode sharpness evaluated through the breadth of the resonance; and the leaky mode intensity.

In this embodiment, advantage is taken of the fact that during QC most samples that pass in a sequence through a measurement system are substantially similar to their neighboring samples in the measurement sequence. This is because samples come in batches from IOX process runs, where most samples within a run are typically substantially identical. This allows for taking a running average of the directly measured knee stress CSk using multiple samples, where the precision of running average is significantly better than the precision of a single direct CSk measurement. The running average can be used to judge whether the values of indirect CSk obtained in the same sequence of measurements (mode spectra) are valid or not. For each sample, the indirect value of CSk is assigned as the measured value of CSk. But this is only considered valid if one or more of the measured parameters (CS, DOL, the indirect CSk) are within an accepted pre-defined allowable deviation of the running average of the one or more parameters. In some cases, it may also be required that the direct CSk value for the same sample deviate by no more than a pre-defined allowable amount.

Furthermore, additional requirements for validity of the measurements can include a requirement that the surface stress CS and the DOL of the spike SP be within pre-defined acceptable deviations from their corresponding running averages, and that selected mode spacings or selected mode spacing ratios be within certain acceptable pre-defined deviations of their corresponding running averages.

If a sudden large change is observed in the directly measured CSk, CS, DOL, the chosen mode spacings or the mode spacing ratios from the corresponding running average, then it can be assumed that the sample does not belong to the same sequence, and additional measurements can be taken. A restart of the running average may also be triggered. Since the benefit of the running average of previous samples is lost, in one embodiment it can be required that only very high quality mode spectra images be accepted for the restart with a direct CSk measurement. This leads to high-quality direct CSk measurements upon restart of the running average. It may also be required that the CSk value assigned to that restart sample be an average of two or more high-quality direct-CSk measurements for that sample.

While some low-quality mode spectra images may be acceptable for measurements of samples that are deemed by the software to belong to the group that produced a running average, mode spectra images that do not meet select quality standards may be rejected from participating in the running average, with the goal of preserving the accuracy and improved precision of the running average for the CSk value.

The benefit of the high precision of the indirect method such as BHOGM is utilized most by such poor-quality mode spectra, for which the direct CSk estimate would have quite poor precision. But the indirect BHOGM will still typically have reasonably good precision, so that in an example, the direct CSk is only used for determining whether the sample belongs to the group for which the indirect CSk method produces a valid value.

In a related embodiment, the running average is used not only to assign a sample as belonging to a group with a certain calibration for the indirect BHOGM, but also to dynamically change the calibration of the indirect BHOGM. As described above, when one or more of the measured parameters of the sample (e.g., direct CSk, CS, DOL) are deemed outside the range of their correspondent running average, the running average is abandoned, and a new running average is started, preferably by imposing a requirement for higher-quality images, and multiple measurements on the first or the first few samples of the new group.

Then a calibration factor for the BHOGM is calculated from the started new running average of direct CSk, and the measured birefringence of the highest-order guided mode, and said calibration factor is used to assign CSk values of subsequent samples based on their measured BHOGM and use of the calibration factor. The calibration factor is improved by forming its own running average, and the benefits of high-precision indirect measurements are reaped for the rest of the samples in the sequence that have similar profiles as the samples that started the new running average.

The indirect method of measuring the knee stress CSk uses the last mode birefringence ($\beta_x$) multiplied by a scaling factor ($F_4$) that is calibrated for specific glass composition, the IOX process conditions and the glass thickness.

$$CS_k^{indirect} = \beta_x \cdot F_4$$

The hybrid method uses the improved direct method to calibrate the scaling factor $F_4$ for various IOX process conditions for improved accuracy and a moving average of $F_4$ to mitigate variability of improved direct CSk for improved precision. In addition to the moving average of $F_4$, a moving average of the fringe spacing ratio, the compressive stress CS and DOL are saved (i.e., stored in memory in the controller 150). In an example, a 15-point moving average is used in one example.

Figure 6:
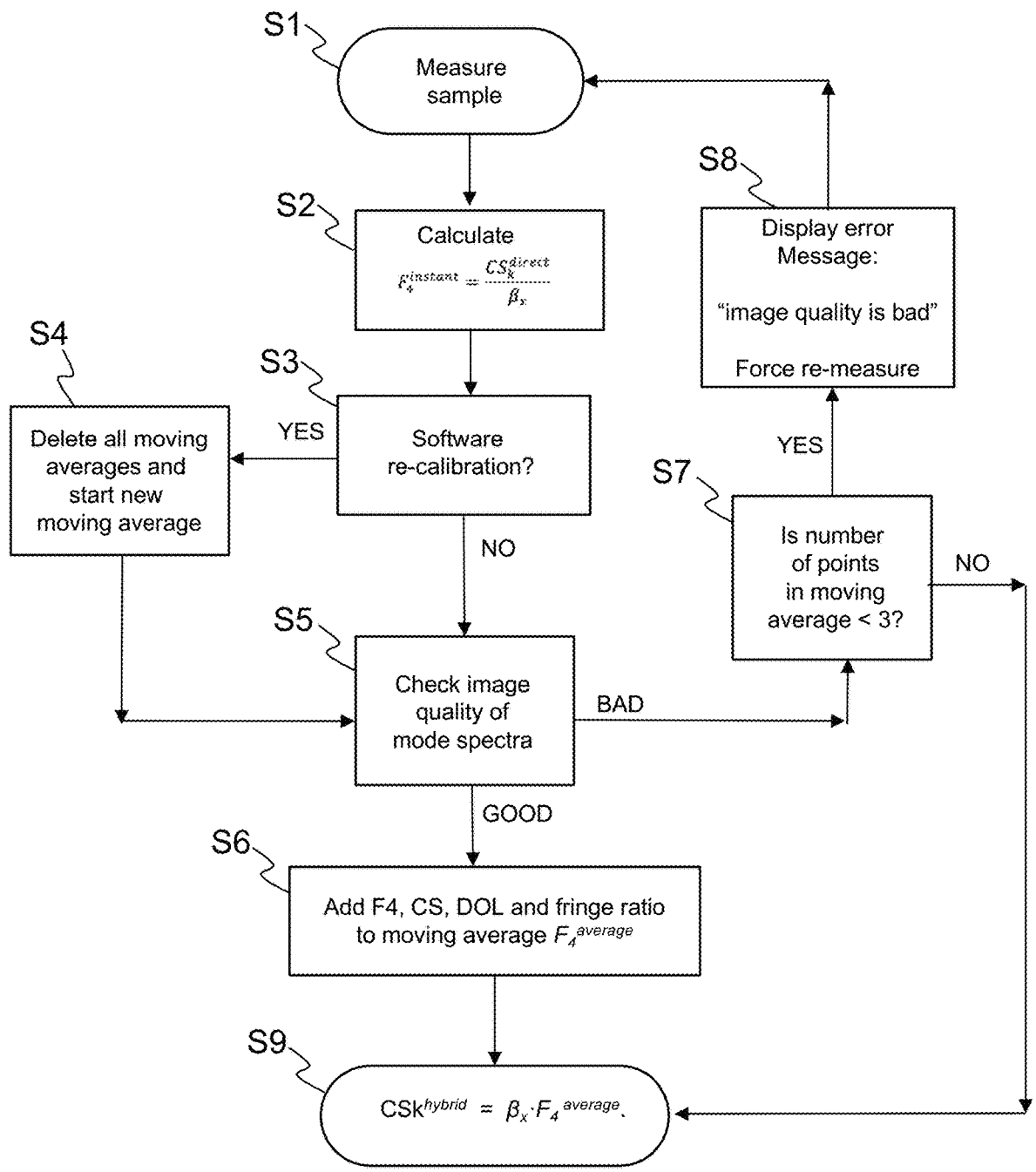
FIG. 6 depicts a flow diagram of an example hybrid method of measuring CSk that combines both direct and indirect measurement methods for determining CSk.

The flow diagram of FIG. 6 with steps S1 through S9 and following description outline the basic calculation and software logic used to carry out the hybrid method of determining CSk based on sample measurements, i.e., the measured mode spectra, which is the first step S1 in the process. The present method, as with all of the methods disclosed herein, can be carried out in the controller 150 using software in the form of instructions embodied in a non-transitory computer-readable medium.

The second step S2 calculates the indirect CSk scaling factor $F_4$, which as noted above, relates the improved direct CSk with the last mode birefringence ($\beta_x$):

$$F_4^{instant} = \frac{CS_k^{direct}}{\beta_x}$$

The third step S3 determines if a re-calibration is needed. If self-recalibration is needed, then the moving averages are deleted in step S4 and a new moving average is started start over. The criteria for this decision-making step can include one or more of the following. The thresholds below are one example implementation.

1) TM(0,1,2) fringe spacing ratio differs from the moving average by more than 0.07 (2nd step only);
2) TM(0,1) fringe spacing differs from the moving average by more than 14 px (1st step only);
3) CS differs from the moving average by more than 70 Mpa;
4) DOL differs from the moving average by more than 0.7 μm;
5) CS differs from the moving average by more than 35 Mpa AND DOL differs from the moving average by more than 0.35 μm;
6) Leaky mode state changes (e.g., moving average has no leaky modes, new measurement has leaky mode or vice versa);
7) Recipe code changes in the software;
8) A change in the conditions of the IOX process (e.g., K, Na bath concentrations, diffusion temperature, etc.).

If no re-calibration is needed, then the fifth step S5 involves checking the image quality of the mode spectra based on select image-quality criteria, which in an example can include one or more of the following:

1) The TIR transition gradient ≤−30 (transition slope must be steep);
2) Average mode width at intensity half max ≤10 pixels;
3) Average mode overshoot ≤25 (i.e., white area after modes must be non-existent or very low intensity).

If the image quality is deemed to be "good," then the sixth step S6 involves updating the moving average, which includes adding $F_4^{instant}$ to a moving average $F_4$ array to establish a moving average $F_4^{average}$. If the image quality is "bad," then the method proceeds to step S7, which inquires whether the array has fewer than 3 data points. If "yes," then the method proceeds to step S8 which cancels the measurement, has the controller issue an error message and sends the method back to step S1 to force a re-measurement of the IOX article (sample). If the image quality is bad and the array has greater than 2 data points, then the method measures the knee stress $CSk^{hybrid}$ of the sample per the last step S9 but does not add $F_4^{instant}$ to the $F_4$ moving average array (i.e., to the moving average $F_4^{average}$), i.e., the method skips the sixth step S6.

For a good mode spectrum image per step 5, then once step S6 is carried out, the method proceeds to step S9 where the hybrid knee stress is calculated via the equation: $CSk^{hybrid}=\beta_x \cdot F_4^{average}$. This hybrid calculation of the knee stress $CSk^{hybrid}$ can result in an accuracy that is within +/−15 MPa and a precision within +/−3 MPa for a sufficient number of samples, e.g., 3 or more samples and preferably 5 or more samples or even 10 or more samples.

Another aspect of the disclosure is a method of measuring a knee stress CSk in chemically strengthened Li-containing glass samples each having a surface and a body and that includes a stress profile having a knee and that defines a waveguide that supports light as guided modes in spike region which has a monotonically decreasing index profile. The method comprises: measuring TE and TM mode spectra for each of the multiple glass samples; for each of the measured TE and TM mode spectra, directly measuring a knee stress $CSk^{direct}$ and also indirectly measuring the knee stress via $CSk^{indirect}=\beta_x \cdot F_4$, where $\beta_x$ is a last-mode birefringence and $F_4$ is a scaling factor; calculating a moving average $F_4^{average}$ for the scaling factor $F_4$ using the directly measured knee stresses $CSk^{direct}$ via the relationship $F_4=CSk^{direct}/\beta_x$; and calculating a hybrid knee stress $CSk^{hybrid}=\beta_x \cdot F_4^{average}$.

QC Methods

Aspects of the disclosure are directed to QC methods of forming the IOX article (glass sample) 10 as disclosed herein.

An example QC method is directed to performing QC of an ion-exchange (IOX) process used to form chemically strengthened Li-containing glass samples 10. The first step in the method includes, for each of a plurality of glass samples formed by the IOX process, measuring the TE and TM mode spectra 250TE and 250TM of the guided modes for each of the glass samples. The next step involves comparing the measured TE and TM mode spectra to reference TE and TM mode spectra of at least one reference glass sample formed using the same IOX process. In an example, the reference samples all have flat surfaces to avoid measurement errors. The next step includes adjusting one or more of the IOX process parameters to maintain the measured TE and TM mode spectra to be within at least one mode spectrum tolerance of the reference TE and TM mode spectra. Example IOX process parameters include: the concentration of the in-diffusing ions (e.g., K+ and Na+), the diffusion temperature and the diffusion time.

The QC methods can also include comparing the TIR-PR transition slopes of the measured samples to those of the reference samples. In this case, the at the least one mode spectrum tolerance comprises the reference slopes, wherein the measured slopes are at least as steep as the reference slopes.

The QC methods can also include comparing the widths of the TM and/or TE fringes 252TM and 252TE of the measured mode spectra to the widths of the TM and/or TE of the reference mode spectra. In this case, the at least one mode spectrum tolerance comprises the reference widths, wherein the measured reference widths are the same size or smaller than the reference widths to indicate that the IOX process is satisfactory. Measured fringe widths greater than the reference fringe widths necessitate making one or more adjustments to the IOX process.

In an example, the QC methods can include determining a knee stress CSk for each glass sample, and then comparing the determined knee stress to a tolerance range on the knee stress and adjusting the IOX process when the determined knee stress falls outside of the tolerance range. In an example, the knee stress tolerance range can be determined from measuring the knee stress of multiple reference glass samples. In one example, the knee stress tolerance range is 70 Mpa while in another example is 50 Mpa.

As part of the QC method, the knee stress can be determined "directly" by calculating $$CSk=[n_{crit}^{TE}-n_{crit}^{TM}]/SOC,$$

where as noted above, $n_{crit}^{TE}$ and $n_{crit}^{TE}$ are respective values of the critical-angle effective index at the TIR-PR transitions for the measured TE and TM mode spectra.

Another example of the method includes using the above-described hybrid calculation of the knee stress that uses both a direct and indirect knee stress calculation.

In an aspect 1, a method of ensuring an accurate measurement of knee stress in a chemically strengthened Li-containing glass sample having a warped surface comprises: capturing a TE mode spectrum and a TM mode spectrum of the glass sample; measuring a TIR-PR slope of light intensity at a TIR-PR transition between a total-internal reflection (TIR) section and a partial-internal reflection (PR) section for one of the TE mode spectrum and TM mode spectrum; measuring a TIR-PR width of the TIR-PR transition for at least one of the TE mode spectrum and TM mode spectrum; comparing the measured TIR-PR slope to a TIR-PR slope threshold and the measured TIR-PR width to a TIR-PR width threshold, wherein the TIR-PR slope threshold and the TIR-PR width threshold are defined by a reference glass sample having a flat surface; and using the TE mode spectrum and the TM mode spectrum to determine the knee stress only if the measured TIR-PR slope is greater than the TIR-PR slope threshold and the measured TIR-PR width is less than the TIR-PR width threshold.

An aspect 2 according to aspect 1, further comprising: forming the glass sample using an ion-exchange (IOX) process that exchanges K+ and Na+ for Li in the Li-containing glass sample to define a spike region and a deep region that define the knee stress; and forming the reference glass sample using the same IOX process as used in forming the glass sample.

An aspect 3 according to aspect 1 or 2, wherein the TE mode spectrum comprises TE mode fringes with a narrowest TE mode fringe and the TM mode spectrum comprises TM mode fringes with a narrowest TM mode fringe, and further comprising: measuring a fringe width of one of the narrowest TE mode fringe and the narrowest TM mode fringe; comparing the measured fringe width to a fringe width threshold as defined by the reference glass sample; and proceeding with the determining of the knee stress only if the measured fringe width is smaller than the fringe width threshold.

An aspect 4 according to any preceding aspect, wherein the TE mode spectrum comprises TE mode fringes with a narrowest TE mode fringe and the TM mode spectrum comprises TM mode fringes with a narrowest TM mode fringe, and further comprising: measuring a contrast of one of the narrowest TE mode fringe and TM mode fringes; and comparing the measured contrast to a contrast threshold as defined by the reference glass sample; and proceeding with the determining of the knee stress if the measured contrast is greater than the contrast threshold.

An aspect 5 according to any preceding aspect, wherein the TE mode spectrum comprises TE mode fringes with a narrowest TE mode fringe and the TM mode spectrum comprises TM mode fringes with a narrowest TM mode fringe, and further comprising: measuring an intensity profile of one of the narrowest TE mode fringe and TM mode fringes; determining an absolute value of a second derivative of the measured intensity profile; and comparing the absolute value of a second derivative to second derivative threshold as defined by the reference glass sample; and proceeding with the determining of the knee stress if the measured absolute value of a second derivative is greater than the second derivative threshold.

An aspect 6 according to any one of aspect 3 through 5, wherein the narrowest TE mode fringe and the narrowest TM mode fringe are the closest of the TE and TM mode fringes to the TIR-PR transition.

An aspect 7 according to any preceding aspect, wherein the capturing of the TE mode spectrum and a TM mode spectrum of the glass sample is performed using a prism-coupling system.

An aspect 8 according to any preceding aspect, wherein the determining of the knee stress CSk comprises using the relationship $CSk=[n_{crit}^{TE}-n_{crit}^{TM}]/SOC$, where $n_{crit}^{TE}$ and $n_{crit}^{TE}$ are respective values of the critical-angle effective index at the TIR-PR transitions for the TE and TM mode spectra.

In an aspect 9, a method of measuring knee stress in a chemically strengthened Li-containing glass sample having a surface and a body and that includes a stress profile having a knee and that defines a waveguide that supports light as guided waves and a leaky mode comprises capturing a TE mode spectrum and a TM mode spectrum of the guide waves and the leaky mode, wherein each mode spectrum has a total internal reflection (TIR) section and a partial-internal reflection (PR) between which resides a TIR-PR transition with a TIR transition location; determining respective TIR-PR transition locations for the TE and TM mode spectra; determining from the TE and TM mode spectra a position of the leaky mode relative to the TIR-PR transitions for the TE and TM mode spectra; determining from the leaky mode position an amount of shift in the TIR-PR position for each of the TM and TE mode spectra as caused by the leaky mode; adding the amount of shift from the measured position of the TIR-PR transition to arrive at a corrected TIR-PR transition location for each of the TM and TE mode spectra; and using the corrected TIR-PR transition locations of the TM and TE mode spectra to determine the knee stress.

An aspect 10 according to aspect 9, wherein the TIR-PR transition is defined by a TIR-PR transition intensity profile, the leaky mode has a leaky mode intensity profile, and wherein the determining of the amount of shift in the TIR-PR position caused by the leaky mode comprises subtracting the leaky mode intensity profile from the TIR-PR transition intensity profile to define a corrected TIR-PR position of the TIR-PR transition.

An aspect 11 according to aspect 10, further comprising characterizing the leaky mode intensity profile by: measuring a breadth of the leaky mode intensity profile; measuring a contrast of the leaky mode intensity profile; and measuring a spacing between the leaky mode and the TIR-PR transition;

An aspect 12 according to aspect 11, wherein determining the position of the leaky mode includes measuring a relative intensity minimum in the partial-internal reflection section and adjacent the TIR-PR transition.

An aspect 13 according to aspect 12, wherein the leaky mode has an intensity profile defined using a digital intensity scale from 0 to 255 using a digital sensor having pixels, and wherein the intensity minima is 6/255 or less and falls within 30 pixels of the TIR-PR transition.

An aspect 14 according to aspect 13, wherein each pixel has a size of between 4 microns and 5 microns.

An aspect 15 according to any one of aspect 12 through 14, wherein the determining of the knee stress CSk comprises using the relationship $CSk=[n_{crit}^{TE}-n_{crit}^{TM}]/SOC$, where $n_{crit}^{TE}$ and $n_{crit}^{TE}$ are respective values of the critical-angle effective index at the TIR-PR transitions for the TE and TM mode spectra.

In an aspect 16, a method of ensuring an accurate measurement of knee stress in a chemically strengthened Li-containing glass sample having a surface and a body and that includes a stress profile having a knee and that defines a waveguide that supports light as guided modes comprises: capturing TE mode spectrum and a TM mode spectrum respectively comprising TE fringes and TM fringes; measuring a slope SLP of a transition between a total-internal reflection and a partial-internal reflection (TIR-PR) for the light supported by the waveguide for each of the TE mode spectrum and the TM mode spectrum; and comparing the slope to a steepness threshold STH and using the slope to determine a location of the TIR-PR transition and using the corrected TIR-PR transition location to determine the knee stress only if the slope is greater than the select steepness threshold STH.

An aspect 17 according to aspect 16, wherein the select steepness threshold STH is defined by measuring mode spectra of a reference glass sample for which an acceptable measurement of the knee stress was obtained.

An aspect 18 according to aspect 16 or 17, wherein the knee stress measurement has a knee stress measurement error, and wherein the steepness threshold STH is selected such the knee stress measurement error is determined to within +/−15 MPa.

An aspect 19 according to aspect 18, wherein the steepness threshold STH is selected such that the knee stress measurement error is within +/−10 MPa.

An aspect 20 according to aspect 19, wherein the steepness threshold STH is selected such that the knee stress measurement error within +/−5 MPa.

An aspect 21 according to any of aspects 16 through 20, wherein each TIR-PR transition has an intensity profile wherein measuring the slope SLP for each of the TIR-PR transition regions for the TE mode spectrum and the TM mode spectrum comprises determining a location of the half-maximum intensity of the TIR-PR transition intensity profile and measuring the slope SLP at the location of the half-maximum intensity of the TIR-PR transition intensity profile.

An aspect 22 according to aspect 21, wherein the TIR-PR transition defines a boundary between a TIR section and a PR section of the given TE or TM mode spectrum, and further comprising performing a best fit to the TIR-PR transition intensity profile that omits an overshoot of the intensity on the TIR side of the TIR-PR transition.

An aspect 23 according to aspect 21 or 22, wherein the TIR-PR transition intensity profile is measured on a digital intensity scale of 0 to 255 units, and wherein the steepness threshold STH=−25/255 as measured on the digital intensity scale.

An aspect 24 according to aspect 21 or 22, wherein the TIR-PR transition intensity profile is measured on a digital intensity scale of 0 to 255 units, and wherein the steepness threshold STH=−10/255 as measured on the digital intensity scale.

An aspect 25 according to any of aspects 21-24, wherein the TIR-PR transition intensity profile is measured on a digital intensity scale of 0 to 255 units, wherein TIR-PR transition defines a boundary between a TIR section and a PR section of the given TE or TM mode spectrum, wherein the TIR-PR transition has an intensity overshoot on the TIR side, and wherein the measurement of the knee stress proceeds only if the intensity overshoot is less than an overshoot tolerance of 30/255 as measured on the digital intensity scale.

An aspect 26 according to aspect 25, wherein the overshoot tolerance is 16/255 as measured on the digital intensity scale.

An aspect 27 according to any of aspects 16-26, further comprising measuring a first width of at least one TE fringe and a second width of at least one TM fringe and proceeding with determining the knee stress from the TE mode spectrum and the TM mode spectrum only if the first and second measured widths are within a select width tolerance.

An aspect 28 according to aspect 27, wherein the width tolerance is defined by measured widths of TE and TM reference fringes of reference mode spectra of a reference glass sample for which an acceptable measurement of the knee stress was obtained.

An aspect 29 according to aspect 27 or 28, wherein TE and TM fringes are measured on a digital intensity scale of 0 to 255 units using a sensor having an array of pixels, and proceeding with determining the knee stress from the TE mode spectrum and the TM mode spectrum only if first and second widths are each smaller than 40 pixels.

An aspect 30 according to aspect 29, wherein each pixel has a dimension of between 4 microns and 5 microns.

An aspect 31 according to aspect 27 or 28, wherein TE and TM fringes are measured on a digital intensity scale of 0 to 255 units using a sensor having an array of pixels, and proceeding with determining the knee stress from the TE mode spectrum and the TM mode spectrum only if first and second widths are each smaller than 8 pixels.

An aspect 32 according to aspect 31, wherein each pixel has a dimension of between 4 microns and 5 microns.

An aspect 33 according to any of aspects 27-32, wherein: measuring the first width of at least one TE fringe comprising measuring first widths of multiple TE fringes and defining an average first width; measuring the second width of at least one TM fringe comprising measuring first widths of multiple TM fringes and defining an average second width; and comparing the average first width and the average second width to the select width tolerance.

An aspect 34 according to aspect 33, wherein TE and TM fringes are measured on a digital intensity scale of 0 to 255 units using a sensor having an array of pixels, and proceeding with determining the knee stress from the TE mode spectrum and the TM mode spectrum only if first and second average widths are each smaller than 40 pixels.

An aspect 35 according to aspect 33, wherein TE and TM fringes are measured on a digital intensity scale of 0 to 255 units using a sensor having an array of pixels, and proceeding with determining the knee stress from the TE mode spectrum and the TM mode spectrum only if first and second average widths are each smaller than 8 pixels.

An aspect 36 according to aspect 35, wherein each pixel has a dimension of between 4 microns and 5 microns.

An aspect 37 according to any of aspects 16 through 36, wherein the determining of the knee stress CSk comprises using the relationship $CSk=[n_{crit}^{TE}-n_{crit}^{TM}]/SOC$, where $n_{crit}^{TE}$ and $n_{crit}^{TE}$ are respective values of the critical-angle effective index at the TIR-PR transitions for the TE and TM mode spectra.

In an aspect 38, a method of measuring a knee stress in chemically strengthened Li-containing glass samples each having a surface and a body and that includes a stress profile having a knee and that defines a waveguide that supports light as guided modes in the spike region which has a monotonically decreasing index profile comprises: measuring TE and TM mode spectra for each of the multiple glass samples; making a direct measurement of the knee stress using the TE and TM mode spectra; making an indirect measurement of the knee stress that employs the direct measurements of the knee stress to define a moving-averaged scaling factor for the indirect measurement; and calculating a hybrid value for the knee stress that using the moving-averaged scaling factor and a birefringence measurement for the sample.

In an aspect 39, a method of measuring a knee stress in chemically strengthened Li-containing glass samples each having a surface and a body and that includes a stress profile having a knee and that defines a waveguide that supports light as guided modes in the spike region which has a monotonically decreasing index profile comprises: measuring TE and TM mode spectra for each of the multiple glass samples, wherein the TE and TM mode spectra have respective TE and TM fringes and respective total-internal reflection and a partial-internal reflection (TIR-PR) transitions associated with a critical angle and that define respective critical angle effective index values $n_{crit}^{TE}$ and $n_{crit}^{TM}$; for each of the measured TE and TM mode spectra, directly measuring a knee stress $CSk^{direct}$ and also indirectly measuring the knee stress via $CSk^{indirect}=\beta_x \cdot F_4$, where $\beta_x$ is a last-mode birefringence and $F_4$ is a scaling factor; calculating a moving average $F_4^{average}$ for the scaling factor $F_4$ using the directly measured knee stresses $CSk^{direct}$ for the multiple samples via the relationship $F_4=CSk^{direct}/\beta_x$; and calculating a hybrid knee stress $CSk^{hybrid}=\beta_x \cdot F_4^{average}$ An aspect 40 according to aspect 39, wherein directly measuring the knee stress $CSk^{direct}$ is performed using the relationship $CSk^{direct}=[n_{crit}^{TE}-n_{crit}^{TM}]/SOC$.

An aspect 41 according to aspect 39 or 40, wherein the moving average includes greater than three values of the scaling factor $F_4$.

An aspect 42 according to any of aspects 39 through 41, further comprising measuring a spacing between adjacent TM fringes and starting a new moving average if the spacing exceeds a fringe spacing tolerance.

An aspect 43 according to any of aspects 39 through 42, further comprising determining a depth of layer DOL for each glass sample, calculating a moving average of the depth of layer DOL, and starting a new moving average of the depth of layer DOL and for the moving average $F_4^{average}$ for the scaling factor $F_4$ if a measured depth of layer DOL differs from the moving average of the depth of layer DOL by more than 0.7 microns.

In an aspect 44, a method of ensuring an accurate measurement of knee stress in a chemically strengthened Li-containing glass sample having a surface and a body and that includes a stress profile having a knee and that defines a waveguide that supports light as guided modes comprises: irradiating the glass sample by directing light from a light source as a light beam through a coupling prism and to the surface of the sample to generate an angular illumination spectrum; detecting the angular illumination spectrum at a digital sensor to capture TE mode spectrum and a TM mode spectrum respectively comprising TE fringes and TM fringes and respective total-internal reflection and a partial-internal reflection (TIR-PR) transitions associated with a critical angle and that define respective critical angle effective index values $n_{crit}^{TE}$ and $n_{crit}^{TM}$, measuring an intensity gradient in the angular illumination spectrum in the vicinity of the TIR-PR transitions; and proceeding with the measurement of the knee stress only if the measured intensity gradient is less than an intensity gradient threshold.

An aspect 45 according to aspect 44, wherein the intensity gradient threshold is determined by measuring an intensity gradient from reference glass sample for which an acceptable measurement of the knee stress was obtained.

An aspect 46 according to aspect 44 or 45, further comprising correcting the intensity gradient to fall within the intensity gradient threshold by adjusting the irradiation of the glass sample.

An aspect 47 according to aspect 46, wherein said correcting comprises inserting a gradient optical filter in the light beam.

An aspect 48 according to any of aspects 44 through 47, wherein the measuring of the intensity gradient is performed by comparing an intensity distribution of the TE and TM mode spectra as detected by the digital sensor to a reference intensity.

An aspect 49 according to any of aspects 44 through 48, wherein the determining of the knee stress CSk comprises using the relationship $CSk=[n_{crit}^{TE}-n_{crit}^{TM}]/SOC$.

In an aspect 50, a method of performing quality control of an ion-exchange (IOX) process used to form chemically strengthened Li-containing glass samples having a surface and a body and that includes a stress profile having a spike and a knee and that defines a waveguide that supports light as guided modes comprises: for each of a plurality of glass samples formed by the IOX process, measuring TE and TM mode spectra of the guided modes for each of the glass samples; comparing the measured TE and TM mode spectra to reference TE and TM mode spectra of at least one reference glass sample formed using the same IOX process and having a flat surface; and adjusting the IOX process to maintain the measured TE and TM mode spectra to be within at least one mode spectrum tolerance of the reference TE and TM mode spectra.

An aspect 51 according to aspect 50, wherein the measured TE and TM mode spectrum comprise total-internal reflection and a partial-internal reflection (TIR-PR) transitions having respective slopes, wherein the reference TE and TM mode spectrum comprise TIR-PIR transitions having respective slopes, and wherein at the least one mode spectrum tolerance comprises the reference slopes, wherein the measured slopes are at least as steep as the reference slopes.

An aspect 52 according to aspect 50 or 51, wherein adjusting the IOX process includes first and second in-diffusing ions, and includes at least one of: adjusting at least one of a first concentration of the first in-diffusing ion and a second concentration of the second in-diffusing ion; adjusting a diffusion temperature; and adjusting as diffusion time.

An aspect 53 according to any of aspects 50 through 52, wherein the first and second in-diffusing ions are K+ and Na+ and are exchanged for Li+ ions in the glass sample.

An aspect 54 according to any of aspects 50 through 53, wherein the measured TE and TM mode spectra comprise respective measured TE and TM mode fringes having respective measured widths, the reference TE and TM mode spectra comprise respective reference TE and TM mode fringes having respective reference widths, and wherein at the least one mode spectrum tolerance comprises the reference widths, wherein the measured reference widths are the same size or smaller than the reference widths.

An aspect 55 according to any of aspects 50 through 54, further comprising: determining a knee stress CSk for each glass sample; and comparing the determined knee stress to tolerance range on the knee stress and adjusting the IOX process when the determined knee stress falls outside of the tolerance range.

An aspect 56 according to aspect 55, wherein the knee stress tolerance range is determined from measuring the knee stress of multiple reference glass samples.

An aspect 57 according to aspect 56, wherein the knee stress tolerance range is 70 Mpa.

An aspect 58 according to aspect 56, wherein the knee stress tolerance range is 50 Mpa.

An aspect 59 according to any of aspects 55-58, wherein the determining of the knee stress CSk comprises calculating $CSk=[n_{crit}^{TE}-n_{crit}^{TM}]/SOC$, where $n_{crit}^{TE}$ and $n_{crit}^{TE}$ are respective values of the critical-angle effective index at the TIR-PR transitions for the TE and TM mode spectra.

An aspect 60 according to any of aspects 55-58, wherein the knee stress CSk for each glass sample comprises: directly measuring a knee stress $CSk^{direct}=[n_{crit}^{TE}-n_{crit}^{TM}]/SOC$, where $n_{crit}^{TE}$ and $n_{crit}^{TE}$ are respective values of the critical-angle effective index at the TIR-PR transitions for the TE and TM mode spectra; indirectly measuring the knee stress via $CSk^{indirect}=\beta_x \cdot F_4$, where $\beta_x$ is a last-mode birefringence and $F_4$ is a scaling factor; calculating a moving average $F_4^{average}$ for the scaling factor $F_4$ using the directly measured knee stresses $CSk^{direct}$ for the multiple samples via the relationship $F_4=CSk^{direct}/\beta_x$; and calculating a hybrid knee stress $CSk=CSk^{hybrid}=\beta_x \cdot H_4^{average}$.

It will be apparent to those skilled in the art that various modifications to the preferred embodiments of the disclosure as described herein can be made without departing from the spirit or scope of the disclosure as defined in the appended claims. Thus, the disclosure covers the modifications and variations provided they come within the scope of the appended claims and the equivalents thereto.

What is claimed is:

1. A method of measuring a knee stress in a chemically strengthened glass sample containing lithium (Li) and having a warped surface, comprising:
    forming the chemically strengthened glass sample using an ion-exchange (IOX) process that exchanges K+ and Na+ for Li in a Li-containing glass sample to form a spike region and a deep region that create the knee stress, and forming a chemically strengthened Li-containing reference glass sample having a flat surface using the same IOX process that forms the chemically strengthened glass sample;
    capturing a TE mode spectrum and a TM mode spectrum of the chemically strengthened glass sample;
    measuring a TIR-PR slope of light intensity at a TIR-PR transition between a total-internal reflection (TIR) section and a partial-internal reflection (PR) section for one of the TE mode spectrum and TM mode spectrum;
    measuring a TIR-PR width of the TIR-PR transition for at least one of the TE mode spectrum and TM mode spectrum;
    comparing the measured TIR-PR slope to a TIR-PR slope threshold and the measured TIR-PR width to a TIR-PR width threshold, wherein the TIR-PR slope threshold and the TIR-PR width threshold are defined by the reference glass sample; and
    using the TE mode spectrum and the TM mode spectrum to determine the knee stress if the measured TIR-PR slope is greater than the TIR-PR slope threshold and the measured TIR-PR width is less than the TIR-PR width threshold.

2. The method according to claim 1, wherein the TE mode spectrum comprises TE mode fringes with a narrowest TE mode fringe and the TM mode spectrum comprises TM mode fringes with a narrowest TM mode fringe, and further comprising:
    measuring a fringe width of one of the narrowest TE mode fringe and the narrowest TM mode fringe;
    comparing the measured fringe width to a fringe width threshold as defined by the reference glass sample; and
    proceeding with the determining of the knee stress only if the measured fringe width is smaller than the fringe width threshold.

3. The method according to claim 1, wherein the TE mode spectrum comprises TE mode fringes with a narrowest TE mode fringe and the TM mode spectrum comprises TM mode fringes with a narrowest TM mode fringe, and further comprising:
    measuring a contrast of one of the narrowest TE mode fringe and TM mode fringes; and
    comparing the measured contrast to a contrast threshold as defined by the reference glass sample; and
    proceeding with the determining of the knee stress if the measured contrast is greater than the contrast threshold.

4. The method according to claim 1, wherein the TE mode spectrum comprises TE mode fringes with a narrowest TE mode fringe and the TM mode spectrum comprises TM mode fringes with a narrowest TM mode fringe, and further comprising:
    measuring an intensity profile of one of the narrowest TE mode fringe and TM mode fringes;
    determining an absolute value of a second derivative of the measured intensity profile; and
    comparing the absolute value of a second derivative to second derivative threshold as defined by the reference glass sample; and
    proceeding with the determining of the knee stress if the measured absolute value of a second derivative is greater than the second derivative threshold.

5. The method according to claim 2, wherein the narrowest TE mode fringe and the narrowest TM mode fringe are the closest of the TE and TM mode fringes to the TIR-PR transition.

6. The method according to claim 1, wherein the capturing of the TE mode spectrum and a TM mode spectrum of the chemically strengthened glass sample is performed using a prism-coupling system.

7. The method according to claim 1, wherein the determining of the knee stress CSk comprises using the relationship $CSk=[n_{crit}^{TE}-n_{crit}^{TM}]/SOC$, where $n_{crit}^{TE}$ and $n_{crit}^{TE}$ are respective values of the critical-angle effective index at the TIR-PR transitions for the TE and TM mode spectra.

8. A method of forming a chemically strengthened Li-containing glass sample, comprising:
    a) forming the chemically strengthened Li-containing glass sample using an ion-exchange (IOX) process that exchanges K+ and Na+ for Li in a Li-containing glass sample to define a stress profile with a spike region and a deep region that define a knee stress and that form a waveguide that supports light as guided waves and a leaky mode;

b) capturing a TE mode spectrum and a TM mode spectrum of the guide waves and the leaky mode, wherein each mode spectrum has a total internal reflection (TIR) section and a partial-internal reflection (PR) between which resides a TIR-PR transition with a TIR transition location;

c) determining respective TIR-PR transition locations for the TE and TM mode spectra;

d) determining from the TE and TM mode spectra a position of the leaky mode relative to the TIR-PR transitions for the TE and TM mode spectra;

e) determining from the leaky mode position an amount of shift in the TIR-PR position for each of the TM and TE mode spectra as caused by the leaky mode;

f) adding the amount of shift from the measured position of the TIR-PR transition to arrive at a corrected TIR-PR transition location for each of the TM and TE mode spectra;

g) using the corrected TIR-PR transition locations of the TM and TE mode spectra to determine the knee stress; and h) if the knee stress falls outside of a knee stress tolerance, adjusting the IOX process of act a) and then repeating acts b) through g) for one or more additional Li-containing glass samples until the knee stress falls within the knee stress tolerance.

9. The method according to claim 8, wherein the TIR-PR transition is defined by a TIR-PR transition intensity profile, the leaky mode has a leaky mode intensity profile, and wherein the determining of the amount of shift in the TIR-PR position caused by the leaky mode comprises subtracting the leaky mode intensity profile from the TIR-PR transition intensity profile to define a corrected TIR-PR position of the TIR-PR transition.

10. The method according to claim 9, further comprising characterizing the leaky mode intensity profile by:
measuring a breadth of the leaky mode intensity profile;
measuring a contrast of the leaky mode intensity profile; and
measuring a spacing between the leaky mode and the TIR-PR transition.

11. The method according to claim 10, wherein determining the position of the leaky mode includes measuring a relative intensity minimum in the partial-internal reflection section and adjacent the TIR-PR transition.

12. The method according to claim 11, wherein the leaky mode has an intensity profile defined using a digital intensity scale from 0 to 255 using a digital sensor having pixels, and wherein the intensity minima is 6/255 or less and falls within 30 pixels of the TIR-PR transition.

13. The method according to claim 11, wherein each pixel has a size of between 4 microns and 5 microns.

14. The method according to claim 8, wherein the determining of the knee stress CSk comprises using the relationship CSk=$[n_{crit}^{TE}-n_{crit}^{TM}]$/SOC, where $n_{crit}^{TE}$ and $n_{crit}^{TE}$ are respective values of the critical-angle effective index at the TIR-PR transitions for the TE and TM mode spectra.

15. A method of forming a chemically strengthened glass sample containing lithium (Li), comprising:
a) forming the chemically strengthened glass sample using an ion-exchange (IOX) process that exchanges K+ and Na+ for Li in a Li-containing glass sample to define a stress profile having a spike region and a deep region that forms a knee stress and a waveguide;

b) optically coupling light into the waveguide using a prism coupling system to capture a TE mode spectrum and a TM mode spectrum respectively comprising TE fringes and TM fringes;

c) measuring a slope SLP of a transition between a total-internal reflection and a partial-internal reflection (TIR-PR) for the light supported by the waveguide for each of the TE mode spectrum and the TM mode spectrum; and d) comparing the slope to a steepness threshold STH and using the slope to determine a location of the TIR-PR transition;

e) using the determined location of the TIR-PR transition to determine the knee stress if the slope is greater than the select steepness threshold STH; and f) if the knee stress falls outside of a knee stress tolerance, adjusting the IOX process of act a) and then repeating acts b) through e) on one or more additional Li-containing glass samples until the knee stress falls within the knee stress tolerance.

16. The method according to claim 15, wherein the select steepness threshold STH is defined by measuring mode spectra of a chemically strengthened Li-containing reference glass sample for which an acceptable measurement of the knee stress was obtained.

17. The method according to claim 15, wherein the knee stress measurement has a knee stress measurement error, and wherein the steepness threshold STH is selected such the knee stress measurement error is determined to within +/−15 MPa.

18. The method according to claim 17, wherein the steepness threshold STH is selected such that the knee stress measurement error is within +/−10 MPa.

19. The method according to claim 18, wherein the steepness threshold STH is selected such that the knee stress measurement error within +/−5 MPa.

20. The method according to claim 15, wherein each TIR-PR transition has an intensity profile wherein measuring the slope SLP for each of the TIR-PR transition regions for the TE mode spectrum and the TM mode spectrum comprises determining a location of the half-maximum intensity of the TIR-PR transition intensity profile and measuring the slope SLP at the location of the half-maximum intensity of the TIR-PR transition intensity profile.

21. The method according to claim 20, wherein the TIR-PR transition defines a boundary between a TIR section and a PR section of the given TE or TM mode spectrum, and further comprising performing a best fit to the TIR-PR transition intensity profile that omits an overshoot of the intensity on the TIR side of the TIR-PR transition.

22. The method according to claim 20, wherein the TIR-PR transition intensity profile is measured on a digital intensity scale of 0 to 255 units, and wherein the steepness threshold STH=−25/255 as measured on the digital intensity scale.

23. The method according to claim 20, wherein the TIR-PR transition intensity profile is measured on a digital intensity scale of 0 to 255 units, and wherein the steepness threshold STH=−10/255 as measured on the digital intensity scale.

24. The method according to claim 20, wherein the TIR-PR transition intensity profile is measured on a digital intensity scale of 0 to 255 units, wherein TIR-PR transition defines a boundary between a TIR section and a PR section of the given TE or TM mode spectrum, wherein the TIR-PR transition has an intensity overshoot on the TIR side, and wherein the measurement of the knee stress proceeds only if the intensity overshoot is less than an overshoot tolerance of 30/255 as measured on the digital intensity scale.

25. The method according to claim 24, wherein the overshoot tolerance is 16/255 as measured on the digital intensity scale.

26. The method according to claim 15, further comprising measuring a first width of at least one TE fringe and a second width of at least one TM fringe and proceeding with determining the knee stress from the TE mode spectrum and the TM mode spectrum only if the first and second measured widths are within a select width tolerance.

27. The method according to claim 26, wherein the width tolerance is defined by measured widths of TE and TM reference fringes of reference mode spectra of a chemically strengthened Li containing reference glass sample for which an acceptable measurement of the knee stress was obtained.

28. The method according to claim 26, wherein TE and TM fringes are measured on a digital intensity scale of 0 to 255 units using a sensor having an array of pixels, and proceeding with determining the knee stress from the TE mode spectrum and the TM mode spectrum only if first and second widths are each smaller than 40 pixels.

29. The method according to claim 28, wherein each pixel has a dimension of between 4 microns and 5 microns.

30. The method according to claim 26, wherein TE and TM fringes are measured on a digital intensity scale of 0 to 255 units using a sensor having an array of pixels, and proceeding with determining the knee stress from the TE mode spectrum and the TM mode spectrum only if first and second widths are each smaller than 8 pixels.

31. The method according to claim 30, wherein each pixel has a dimension of between 4 microns and 5 microns.

32. The method according to claim 26, wherein:
measuring the first width of at least one TE fringe comprising measuring first widths of multiple TE fringes and defining an average first width;
measuring the second width of at least one TM fringe comprising measuring first widths of multiple TM fringes and defining an average second width; and
comparing the average first width and the average second width to the select width tolerance.

33. The method according to claim 32, wherein TE and TM fringes are measured on a digital intensity scale of 0 to 255 units using a sensor having an array of pixels, and proceeding with determining the knee stress from the TE mode spectrum and the TM mode spectrum only if first and second average widths are each smaller than 40 pixels.

34. The method according to claim 32, wherein TE and TM fringes are measured on a digital intensity scale of 0 to 255 units using a sensor having an array of pixels, and proceeding with determining the knee stress from the TE mode spectrum and the TM mode spectrum only if first and second average widths are each smaller than 8 pixels.

35. The method according to claim 34, wherein each pixel has a dimension of between 4 microns and 5 microns.

36. The method according to claim 15, wherein the determining of the knee stress CSk comprises using the relationship $CSk=[n_{crit}^{TE}-n_{crit}^{TM}]/SOC$, where $n_{crit}^{TE}$ and $n_{crit}^{TE}$ are respective values of the critical-angle effective index at the TIR-PR transitions for the TE and TM mode spectra.

37. A method of forming chemically strengthened glass samples, comprising:
a) performing an ion-exchange (IOX) process that exchanges K+ and Na+ for Li in a plurality of Li-containing glass samples to form a plurality of chemically strengthened glass samples each having a spike region and a deep region that form a waveguide and that create a knee stress;
b) measuring TE and TM mode spectra for each of the chemically strengthened glass samples;
c) making a direct measurement of the knee stress of the chemically strengthened glass samples the using the TE and TM mode spectra;
d) making an indirect measurement of the knee stress of the chemically strengthened glass samples by using a last-mode birefringence as obtained using the direct measurement of the knee stress to define a moving-averaged scaling factor for the indirect measurement;
e) calculating a hybrid value for the knee stress that uses the moving-averaged scaling factor and a birefringence measurement for the chemically strengthened glass samples; and
f) if the knee stress falls outside of a knee stress tolerance, adjusting the IOX process of act a) and then repeating acts b) through e) on one or more additional Li-containing glass samples until the hybrid value of the knee stress falls within the knee stress tolerance.

38. A method of forming chemically strengthened glass samples, comprising:
a) performing an ion-exchange (IOX) process that exchanges K+ and Na+ for Li in a plurality of Li-containing glass samples to form a plurality of chemically strengthened glass samples each having a spike region and a deep region that form a waveguide and that create a knee stress;
b) measuring TE and TM mode spectra for each of the chemically strengthened glass samples, wherein the TE and TM mode spectra have respective TE and TM fringes and respective total-internal reflection and a partial-internal reflection (TIR-PR) transitions associated with a critical angle and that define respective critical angle effective index values $n_{crit}^{TE}$ and $n_{crit}^{TM}$;
c) for each of the measured TE and TM mode spectra, directly measuring a knee stress $CSk^{direct}$ and also indirectly measuring the knee stress via $CSk^{indirect}=\beta_x \cdot F_4$, where $\beta_x$ is a last-mode birefringence and $F_4$ is a scaling factor;
d) calculating a moving average $F_4^{average}$ for the scaling factor $F_4$ using the directly measured knee stresses $CSk^{direct}$ for the multiple samples via the relationship $F_4=CSk^{direct}/\beta_x$; and
e) calculating a hybrid knee stress $CSk^{hybrid}=\beta_x \cdot F_4^{average}$; and
f) if the knee stress falls outside of a knee stress tolerance, adjusting the IOX process of act a) and then repeating acts b) through e) on one or more additional Li-containing glass samples until the hybrid value of the knee stress falls within the knee stress tolerance.

39. The method according to claim 38, wherein directly measuring the knee stress $CSk^{direct}$ is performed using the relationship $CSk^{direct}=[n_{crit}^{TE}-n_{crit}^{Tm}]/SOC$.

40. The method according to claim 38, wherein the moving average includes greater than three values of the scaling factor $F_4$.

41. The method according to claim 38, further comprising measuring a spacing between adjacent TM fringes and starting a new moving average if the spacing exceeds a fringe spacing tolerance.

42. The method according to claim 38, further comprising determining a depth of layer DOL for each chemically strengthened glass sample, calculating a moving average of the depth of layer DOL, and starting a new moving average of the depth of layer DOL and for the moving average $F_4^{average}$ for the scaling factor $F_4$ if a measured depth of layer DOL differs from the moving average of the depth of layer DOL by more than 0.7 microns.

43. A method of forming a chemically strengthened Li-containing glass sample, comprising:
    a) performing an ion-exchange (IOX) process on a glass sample containing Li to form the chemically strengthened Li-containing glass samples, with each of the chemically strengthened Li-containing glass samples comprising a stress profile having a knee stress and that forms a waveguide that supports light as guided modes;
    b) irradiating the chemically strengthened Li-containing glass sample by directing light from a light source as a light beam through a coupling prism and to the surface of the sample to generate an angular illumination spectrum representative of the guided modes;
    c) detecting the angular illumination spectrum at a digital sensor to capture a TE mode spectrum and a TM mode spectrum respectively comprising TE fringes and TM fringes and respective total-internal reflection and a partial-internal reflection (TIR-PR) transitions associated with a critical angle and that define respective critical angle effective index values $n_{crit}^{TE}$ and $n_{crit}^{TM}$,
    d) measuring an intensity gradient in the angular illumination spectrum in the vicinity of the TIR-PR transitions;
    e) proceeding with a measurement of the knee stress if the measured intensity gradient is less than an intensity gradient threshold; and
    f) if the knee stress falls outside of a knee stress tolerance, adjusting the IOX process of act a) and then repeating acts b) through e) on one or more additional Li-containing glass samples until the knee stress falls within the knee stress tolerance.

44. The method according to claim 43 wherein the intensity gradient threshold is determined by measuring an intensity gradient from reference glass sample for which an acceptable measurement of the knee stress was obtained.

45. The method according to claim 43, further comprising correcting the intensity gradient to fall within the intensity gradient threshold by adjusting the irradiation of the glass sample.

46. The method according to claim 45, wherein said correcting comprises inserting a gradient optical filter in the light beam.

47. The method according to claim 43, wherein the measuring of the intensity gradient is performed by comparing an intensity distribution of the TE and TM mode spectra as detected by the digital sensor to a reference intensity.

48. The method according to claim 43, wherein the determining of the knee stress CSk comprises using the relationship $CSk=[n_{crit}^{TE}-n_{crit}^{TM}]/SOC$.

49. A method of forming chemically strengthened Li-containing glass samples comprising the following acts:
    a) performing an ion-exchange (IOX) process on a set of glass samples containing Li to form the chemically strengthened Li-containing glass samples, with each of the chemically strengthened Li-containing glass samples comprising a stress profile that forms a waveguide that supports light as guided modes;
    b) measuring TE and TM mode spectra of the guided modes for each of the chemically strengthened Li-containing glass samples;
    c) comparing the measured TE and TM mode spectra to reference TE and TM mode spectra of at least one reference glass sample having a flat surface and formed using the same IOX process of act a) used to form the chemically strengthened Li-containing glass samples; and
    d) if the TE and TM mode spectra exceeds a mode spectra tolerance based on the reference TE and TM mode spectra, adjusting the IOX process of act a) and repeating acts b) and c) on a new set of glass samples containing Li until the measured TE and TM mode spectra are within the mode spectra tolerance.

50. The method according to claim 49, wherein the measured TE and TM mode spectra comprise total-internal reflection and a partial-internal reflection (TIR-PR) transitions having respective slopes, wherein the reference TE and TM mode spectra comprise TIR-PIR transitions having respective slopes, and wherein at the mode spectra tolerance comprises the reference slopes, wherein the measured slopes are at least as steep as the reference slopes.

51. The method according to claim 49, wherein adjusting the IOX process includes first and second in-diffusing ions, and includes at least one of:
    adjusting at least one of a first concentration of the first in-diffusing ion and a second concentration of the second in-diffusing ion;
    adjusting a diffusion temperature; and
    adjusting as diffusion time.

52. The method according to claim 49, wherein the first and second in-diffusing ions are K+ and Na+ and are exchanged for Li+ ions in the glass sample.

53. The method according to claim 49 wherein the measured TE and TM mode spectra comprise respective measured TE and TM mode fringes having respective measured widths, the reference TE and TM mode spectra comprise respective reference TE and TM mode fringes having respective reference widths, and wherein at the mode spectra tolerance comprises the reference widths, wherein the measured reference widths are the same size or smaller than the reference widths.

54. The method according to claim 49, further comprising:
    determining a knee stress CSk for each chemically strengthened Li-containing glass sample; and
    comparing the determined knee stress to tolerance range on the knee stress and adjusting the IOX process of act a) and repeating acts b) and c) on the new set of glass samples containing Li when the determined knee stress falls outside of the tolerance range.

55. The method according to claim 54, wherein the knee stress tolerance range is determined from measuring the knee stress of multiple reference glass samples.

56. The method according to claim 55, wherein the knee stress tolerance range is 70 Mpa.

57. The method according to claim 55, wherein the knee stress tolerance range is 50 Mpa.

58. The method according to claim 54, wherein the determining of the knee stress CSk comprises calculating $CSk=[n_{crit}^{TE}-n_{crit}^{TM}]/SOC$, where $n_{crit}^{TE}$ and $n_{crit}^{TE}$ are respective values of the critical-angle effective index at the TIR-PR transitions for the TE and TM mode spectra.

59. The method according to claim 54, wherein the knee stress CSk for each chemically strengthened Li-containing glass sample comprises:
    directly measuring a knee stress $CSk^{direct}=[n_{crit}^{TE}-n_{crit}^{TM}]/SOC$, where $n_{crit}^{TE}$ and $n_{crit}^{TE}$ are respective values of the critical-angle effective index at the TIR-PR transitions for the TE and TM mode spectra;

indirectly measuring the knee stress via $CSk^{indirect}=\beta_x \cdot F_4$, where $\beta^x$ is a last-mode birefringence and $F_4$ is a scaling factor;

calculating a moving average $F_4^{average}$ for the scaling factor $F_4$ using the directly measured knee stresses $CSk^{direct}$ for the multiple samples via the relationship $F_4=CSk^{direct}/\beta_x$; and calculating a hybrid knee stress $CSk=CSk^{hybrid}=\beta_x \cdot F_4^{average}$.

* * * * *

UNITED STATES PATENT AND TRADEMARK OFFICE
CERTIFICATE OF CORRECTION

PATENT NO. : 10,900,850 B2  
APPLICATION NO. : 16/015776  
DATED : January 26, 2021  
INVENTOR(S) : Ryan Claude Andrews et al.

It is certified that error appears in the above-identified patent and that said Letters Patent is hereby corrected as shown below:

On the Title Page

In Column 2, item (56), Other Publications, Line 1, delete "Invitiation" and insert -- Invitation --, therefor.

In the Claims

In Column 32, Line 56, Claim 7, delete "$n_{crit}^{TE}$" and insert -- $n_{crit}^{TM}$ --, therefor.

In Column 33, Line 58, Claim 14, delete "$n_{crit}^{TE}$" and insert -- $n_{crit}^{TM}$ --, therefor.

In Column 35, Line 60, Claim 36, delete "$n_{crit}^{TE}$" and insert -- $n_{crit}^{TM}$ --, therefor.

In Column 36, Line 56, Claim 39, delete "$n_{crit}^{Tm}$]" and insert -- $n_{crit}^{TM}$] --, therefor.

In Column 37, Line 24, Claim 43, delete "$n_{crit}^{TM}$," and insert -- $n_{crit}^{TM}$; --, therefor.

In Column 38, Line 58, Claim 58, delete "$n_{crit}^{TE}$" and insert -- $n_{crit}^{TM}$ --, therefor.

In Column 38, Line 65, Claim 59, delete "$n_{crit}^{TE}$" and insert -- $n_{crit}^{TM}$ --, therefor.

In Column 39, Line 2, Claim 59, delete "$\beta^x$" and insert -- $\beta_x$ --, therefor.

Signed and Sealed this  
First Day of June, 2021

Drew Hirshfeld  
*Performing the Functions and Duties of the*  
*Under Secretary of Commerce for Intellectual Property and*  
*Director of the United States Patent and Trademark Office*